(12) United States Patent
Carroux et al.

(10) Patent No.: US 11,903,559 B2
(45) Date of Patent: Feb. 20, 2024

(54) SURGEON CONTROLLED ENDOSCOPE DEVICE AND METHOD

(71) Applicant: Gyrus ACMI, Inc., Southborough, MA (US)

(72) Inventors: Alexander Carroux, Waltham, MA (US); Kurt G. Shelton, Bedford, MA (US); Christopher A. Cook, Laguna Niguel, CA (US)

(73) Assignee: Gyrus ACMI, Inc., Westborough, MA (US)

( * ) Notice: Subject to any disclaimer, the term of this patent is extended or adjusted under 35 U.S.C. 154(b) by 100 days.

(21) Appl. No.: 16/059,471

(22) Filed: Aug. 9, 2018

(65) Prior Publication Data
US 2018/0344134 A1 Dec. 6, 2018

Related U.S. Application Data

(63) Continuation of application No. 14/177,408, filed on Feb. 11, 2014, now Pat. No. 10,076,231, which is a
(Continued)

(51) Int. Cl.
*A61B 1/00* (2006.01)
*A61B 17/221* (2006.01)

(52) U.S. Cl.
CPC ........ *A61B 1/00133* (2013.01); *A61B 17/221* (2013.01)

(58) Field of Classification Search
CPC . A61B 17/221; A61B 17/32056; A61B 17/22; A61B 1/00085; A61B 2017/00358;
(Continued)

(56) References Cited

U.S. PATENT DOCUMENTS

| 3,605,725 A | 9/1971 | Bentov |
| 5,573,530 A | 11/1996 | Fleury et al. |

(Continued)

FOREIGN PATENT DOCUMENTS

| CN | 1861011 A | 11/2006 |
| CN | 1886087 A | 12/2006 |

(Continued)

OTHER PUBLICATIONS

"U.S. Appl. No. 14/092,199, Advisory Action dated Dec. 1, 2016", 3 pgs.

(Continued)

*Primary Examiner* — Alexandra L Newton
(74) *Attorney, Agent, or Firm* — Schwegman Lundberg & Woessner, P.A.

(57) ABSTRACT

A medical apparatus including an endoscopic tool including first and second members longitudinally slidable relative to each other; and a control connected to a proximal end of the endoscopic tool. The control includes a housing and an actuation mechanism. The actuation mechanism is longitudinally slidably connected to the housing. The actuation mechanism has the first member and/or the second member connected thereto. The housing includes a connector configured to removably connect the housing to a control section of an endoscope.

11 Claims, 18 Drawing Sheets

Related U.S. Application Data continuation-in-part of application No. 14/092,199, filed on Nov. 27, 2013, now Pat. No. 10,058,234.

(60) Provisional application No. 61/814,498, filed on Apr. 22, 2013.

(58) Field of Classification Search
CPC ............ A61B 1/00066; A61B 1/00131; A61B 1/0014; A61B 1/0051; A61B 1/0052; A61B 1/012; A61B 1/0125
See application file for complete search history.

(56) References Cited

U.S. PATENT DOCUMENTS

| | | | |
|---|---|---|---|
| 5,865,800 A | | 2/1999 | Mirarchi et al. |
| 5,976,121 A | | 11/1999 | Matern et al. |
| 6,258,083 B1* | | 7/2001 | Daniel .............. A61B 1/00098 606/15 |
| 6,315,774 B1* | | 11/2001 | Daniel .................. A61B 18/24 606/7 |
| 6,676,668 B2 | | 1/2004 | Mercereau et al. |
| 6,764,499 B2 | | 7/2004 | Honey et al. |
| 8,100,903 B2 | | 1/2012 | Kennedy, II |
| 8,211,115 B2 | | 7/2012 | Cheng et al. |
| 10,058,234 B2 | | 8/2018 | Carroux et al. |
| 10,076,231 B2 | | 9/2018 | Carroux et al. |
| 2005/0119527 A1 | | 6/2005 | Banik et al. |
| 2007/0100254 A1* | | 5/2007 | Murakami ............ A61B 34/72 600/564 |
| 2007/0167679 A1 | | 7/2007 | Miyamoto et al. |
| 2008/0188868 A1 | | 8/2008 | Weitzner et al. |
| 2012/0004502 A1* | | 1/2012 | Weitzner ............ A61B 1/00039 600/102 |
| 2012/0165829 A1 | | 6/2012 | Chen et al. |
| 2013/0172673 A1 | | 7/2013 | Kennedy, II et al. |
| 2014/0223701 A1* | | 8/2014 | Bean .................. A61B 1/00133 24/483 |
| 2014/0316202 A1 | | 10/2014 | Carroux et al. |
| 2014/0316203 A1 | | 10/2014 | Carroux et al. |

FOREIGN PATENT DOCUMENTS

| | | |
|---|---|---|
| CN | 101594816 A | 12/2009 |
| CN | 105392412 A | 3/2016 |
| CN | 105392412 B | 6/2017 |
| DE | 102009014178 A1 | 9/2010 |
| EP | 2988652 A1 | 3/2016 |
| EP | 2988652 B1 | 9/2017 |
| EP | 3272269 A1 | 1/2018 |
| EP | 3272269 B1 | 9/2021 |
| JP | 2004358012 A | 12/2004 |
| JP | 2007117394 A | 5/2007 |
| JP | 2007151595 A | 6/2007 |
| JP | 2016522704 A | 8/2016 |
| JP | 6290376 B2 | 3/2018 |
| WO | WO-2008070556 A1 | 6/2008 |
| WO | WO-2014091408 A1 | 6/2014 |
| WO | WO-2014164541 A1 | 10/2014 |
| WO | WO-2014174378 A1 | 10/2014 |

OTHER PUBLICATIONS

"U.S. Appl. No. 14/092,199, Final Office Action dated Oct. 3, 2016", 12 pgs.
"U.S. Appl. No. 14/092,199, Non Final Office Action dated Apr. 4, 2016", 9 pgs.
"U.S. Appl. No. 14/092,199, Non Final Office Action dated Dec. 11, 2017", 16 pgs.
"U.S. Appl. No. 14/092,199, Notice of Allowance dated Apr. 27, 2018", 7 pgs.
"U.S. Appl. No. 14/092,199, Response filed Mar. 12, 2018 to Non Final Office Action dated Dec. 11, 2017", 13 pgs.
"U.S. Appl. No. 14/092,199, Response filed Jul. 5, 2016 to Non Final Office Action dated Apr. 4, 2016", 10 pgs.
"U.S. Appl. No. 14/092,199, Response filed Sep. 25, 2015 to Restriction Requirement dated Aug. 27, 2015", 10 pgs.
"U.S. Appl. No. 14/092,199, Response filed Nov. 18, 2016 to Final Office Action dated Oct. 3, 2016", 13 pgs.
"U.S. Appl. No. 14/092,199, Restriction Requirement dated Aug. 27, 2015", 8 pgs.
"U.S. Appl. No. 14/177,408, Final Office Action dated Apr. 7, 2017", 8 pgs.
"U.S. Appl. No. 14/177,408, Non Final Office Action dated Jun. 23, 2016", 10 pgs.
"U.S. Appl. No. 14/177,408, Non Final Office Action dated Dec. 20, 2017", 11 pgs.
"U.S. Appl. No. 14/177,408, Notice of Allowance dated May 17, 2018", 8 pgs.
"U.S. Appl. No. 14/177,408, Response filed Feb. 3, 2016 to Restriction Requirement dated Dec. 15, 2015", 9 pgs.
"U.S. Appl. No. 14/177,408, Response filed Mar. 20, 2018 to Non Final Office Action dated Dec. 20, 2017", 12 pgs.
"U.S. Appl. No. 14/177,408, Response filed Jul. 5, 2017 to Final Office Action dated Apr. 7, 2017", 11 pgs.
"U.S. Appl. No. 14/177,408, Response filed Nov. 18, 2016 to Non Final Office Action dated Jun. 23, 2016", 11 pgs.
"U.S. Appl. No. 14/177,408, Restriction Requirement dated Dec. 15, 2015", 8 pgs.
"Chinese Application Serial No. 201480035752.X, Office Action dated Dec. 5, 2016", with English translation of claims, 15 pgs.
"Chinese Application Serial No. 201480035752.X, Response filed Jan. 22, 2017 to Office Action dated Dec. 5, 2016", with machine translation and English translation of claims, 15 pgs.
"European Application Serial No. 14708671.4, Response to Communication pursuant to Rules 161(1) and 162 EPC filed Jun. 15, 2016", 18 pgs.
"European Application Serial No. 17183319.7, Extended European Search Report dated Dec. 21, 2017", 6 pgs.
"European Application Serial No. 17183319.7, Response filed Jul. 6, 2018 to Extended European Search Report dated Dec. 21, 2017", 13 pgs.
"International Application Serial No. PCT/IB2014/058925, International Preliminary Report on Patentability dated Nov. 5, 2015", 12 pgs.
"International Application Serial No. PCT/IB2014/058925, International Search Report dated Jul. 10, 2014", 5 pgs.
"International Application Serial No. PCT/IB2014/058925, Written Opinion dated Jul. 10, 2014", 10 pgs.
"Japanese Application Serial No. 2016-509564, Notification of Reasons for Refusal dated Mar. 3, 2017", 6 pgs.
"Japanese Application Serial No. 2016-509564, Notification of Reasons for Refusal dated Sep. 28, 2017", 6 pgs.
"Japanese Application Serial No. 2016-509564, Response filed Jun. 5, 2017 to Notification of Reasons for Refusal dated Mar. 3, 2017", 9 pgs.
"Japanese Application Serial No. 2016-509564, Response filed Nov. 24, 2017 to Notification of Reasons for Refusal dated Sep. 28, 2017", 9 pgs.

* cited by examiner

SURGEON CONTROLLED ENDOSCOPE DEVICE AND METHOD

CROSS REFERENCE TO RELATED APPLICATION

The present application is a continuation of a U.S. Non-Provisional application Ser. No. 14/177,408, filed on Feb. 11, 2014, which is a continuation-in-part of U.S. application Ser. No. 14/092,199 filed Nov. 27, 2013 which claims priority to U.S. Provisional Patent Application No. 61/814,498 filed Apr. 22, 2013, the entire contents of each of these applications are hereby incorporated by reference.

BACKGROUND

Technical Field

The exemplary and non-limiting embodiments relate generally to an endoscope and, more particularly, to an apparatus used with an endoscope.

Brief Description of Prior Developments

U.S. Pat. No. 6,764,499 discloses a medical device with a basket. U.S. Pat. No. 8,211,115 discloses a variable size retrieval basket.

SUMMARY

The following summary is merely intended to be exemplary. The summary is not intended to limit the scope of the claims.

In accordance with one aspect, a medical apparatus includes an endoscopic tool including first and second members longitudinally slidable relative to each other; and a control connected to a proximal end of the endoscopic tool. The control includes a housing and an actuation mechanism. The actuation mechanism is longitudinally slidably connected to the housing. The actuation mechanism has the first member and/or the second member connected thereto. The housing includes a connector configured to removably connect the housing to a control section of an endoscope.

In accordance with another aspect, an example method comprises inserting a distal end of an endoscopic device into a working channel of an endoscope, where the endoscopic device comprises an endoscopic tool, where the endoscopic tool comprises first and second members which are longitudinally slidable relative to each other; and removably connecting a proximal end of the endoscopic device to a control section of the endoscope, where the proximal end comprises a housing and an actuation mechanism, where the actuation mechanism is slidably connected to the housing, where the actuation mechanism has the first member and/or the second member connected thereto, and where the housing comprises a connector which removably connects the housing to the control section of the endoscope.

In accordance with another aspect, an example method comprises providing an endoscopic tool, where the endoscopic tool comprises first and second members which are longitudinally slidable relative to each other; and connecting a control to a proximal end of the endoscopic tool, where the control comprises a housing and an actuation mechanism, where the actuation mechanism is longitudinally slidably connected to the housing, where the actuation mechanism has the first member and/or the second member connected thereto, and where the housing comprises a connector configured to removably connect the housing to a control section of an endoscope.

BRIEF DESCRIPTION OF THE DRAWINGS

The foregoing aspects and other features are explained in the following description, taken in connection with the accompanying drawings, wherein.

DETAILED DESCRIPTION OF EMBODIMENTS

Figure 1:
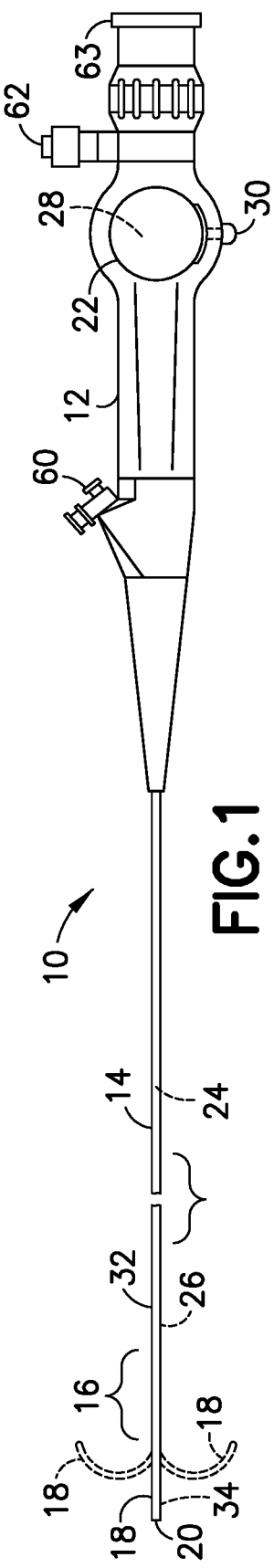
FIG. 1 is a side view of an endoscope.

Referring to FIG. 1, there is shown a side elevation view of an apparatus 10 incorporating features in an example embodiment. Although the present invention will be described with reference to the embodiments shown in the drawings, it should be understood that the present invention can be embodied in many alternate forms of embodiments. In addition, any suitable size, shape or type of elements or materials could be used.

The apparatus 10 in this example is an endoscope medical device configured to be partially inserted into a patient's body, such as in through the patient's urethra for example. The endoscope 10 generally comprises a control section 12 and a flexible or semi-flexible shaft connected to the control section 12. The control section 12 forms a handle for the apparatus. The shaft 14 includes a passive deflection section 16 and an active deflection section (bending section) 18 at the distal end of the shaft 14. A control system 22 to control the active deflection section 18 extends from the control section 12 to the active deflection section 18. The control system 22 generally comprises bending control wires, wire sheaths, and an actuator 28. The wires are connected to the actuator 28 at one end and are connected to the active deflection section 18 at a second end.

In the example embodiment shown, the control section 12 has a user operated slide or lever (control lever) 30. The lever 30 is connected to the actuator 28. The actuator 28 is adapted to pull and release the wires of the control system 22. When the lever 30 is moved by the user, the actuator 28 is moved. The actuator 28 may be, for example, a drum or pulley rotatably connected to the control section 12 to pull one wire while releasing the other. In an alternate embodiment, the actuator may be any suitable type of device, such as a rocker arm adapted to pull and release the wires of the control system 22. In another alternate embodiment, where the control system may have two or more pairs of control wires, the control section will have additional actuators and corresponding controls to drive the additional pairs of bending control wires. In still other alternate embodiments, the control section may have knobs with rack and pinion mechanisms or other suitable user operated controls for the control system.

The shaft 14 is cantilevered from the control section 12. The flexible shaft 14 includes the bending control wires of the control system 22, a fiber optic image bundle, a fiber optic illumination bundle, and a working channel. A port 60 for inserting instruments into the working channel 24 of the shaft is located on the control section 12. The control section 12 also has a light source post 62 for connecting a light source (not shown) to the illumination bundle. In addition, the control section 12 has an eyepiece 63 for a user to view an image transmitted by the image bundle from the front end 20. In alternate embodiments, the flexible shaft may house different systems within. The shaft 14 generally comprises a frame 26, a cover 32 and an objective head 34.

Figure 2:
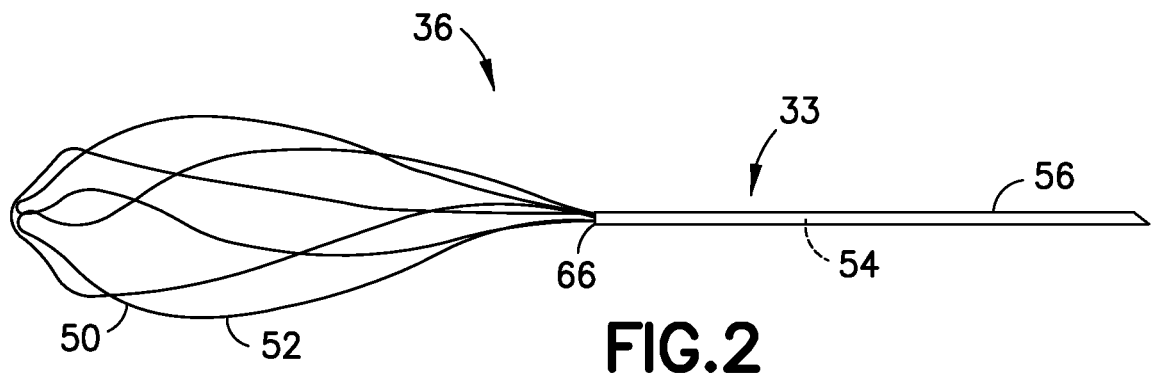
FIG. 2 is a side view of a distal end of an endoscopic tool of an endoscopic device.
Figure 3A:
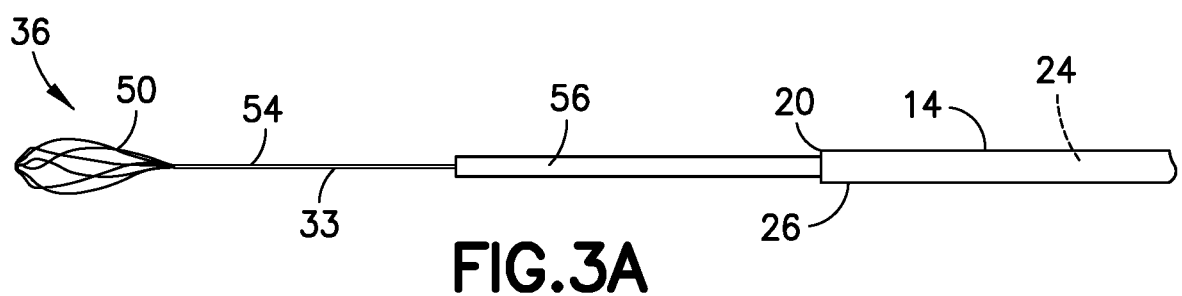
FIG. 3A is a side view illustrating extension of the tool shown in FIG. 2 from the distal end of the endoscope shown in FIG. 1.

Referring also to FIGS. 2-3A, a distal end of an endoscopic tool 36 is shown. The tool 36 is attached to the apparatus 10 and is configured to extend out of the distal end 20 of the shaft 14 from the working channel 24. The tool 36, in this example, is a Surgeon Controlled Basket Device (SCBD). The tool 36 includes an assembly 33 which comprises a basket device 50 and a sheath 56. The basket device 50 comprises a basket section 52 at a distal end, and a shaft section 54 extending through the sheath 56 to a proximal end of the tool 36. The shaft section 54 functions as a control wire for moving the basket section 52. The sheath 56 and basket device 50 are longitudinally movable relative to each other to move the basket device 50 between a forward position and a rearward position relative to the sheath 56. FIGS. 2 and 3A show the shaft section (control wire) 54 moved forward relative to the sheath 56 such that the basket section 52 is located out from a front end aperture 66 of the sheath 56. In the forward position of the sheath 56 on the basket device 50, the basket section 52 is located inside the sheath 56; the basket section 52 being collapsed by the sheath 56 into a smaller shape to fit inside the sheath 56.

Figure 4A:
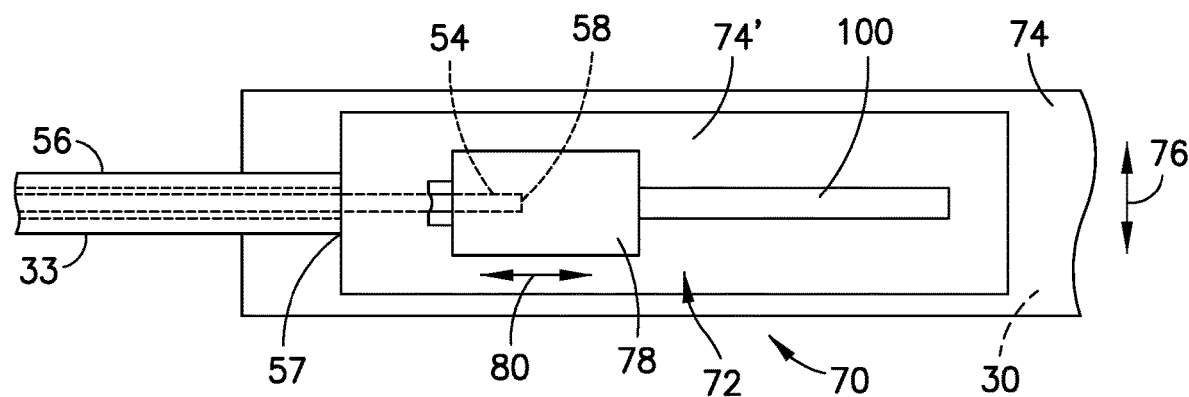
FIG. 4A is a plan view of a control of the endoscopic device shown in FIG. 2 with the slider/actuation mechanism in a first position.
Figure 4B:
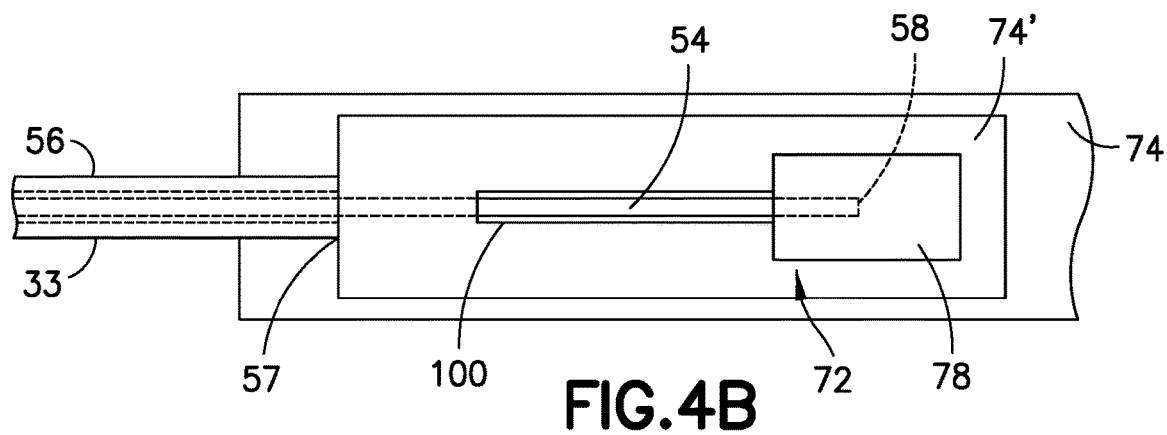
FIG. 4B is a plan view as in FIG. 4A with the slider/actuation mechanism in a second position.
Figure 6:
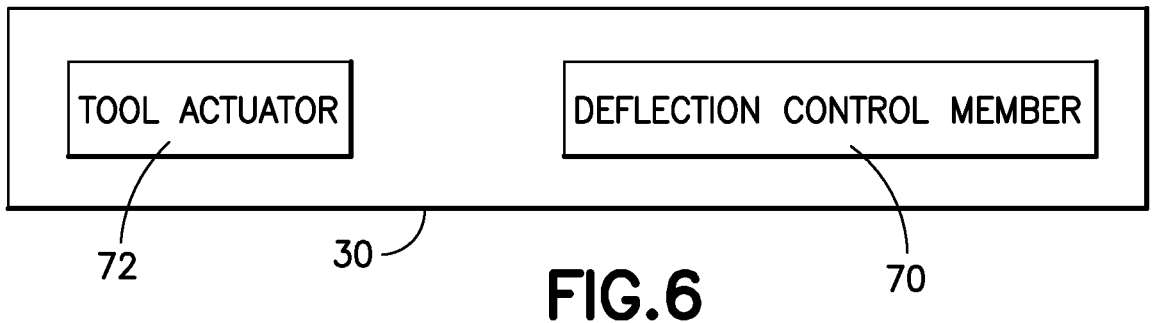
FIG. 6 is a schematic illustration of combined features of the invention.

Referring also to FIGS. 4A, 4B and 6, in this example embodiment the lever 30 is both a deflection control member 70 for the actuator 28 and a tool actuator for the tool 36. A frame 74 of the lever 30 is connected to the actuator 28 to be able to rotate the actuator 28 as the lever 30 is rotated forward and backward as indicated by arrow 76 in FIG. 7. The tool actuator 72 comprises a slider member 78, or actuation mechanism, which is movably mounted on a slit 100 of a tool actuator frame 74' to be able to slide laterally as indicated by arrow 80. The proximal end 58 of the shaft section 54 is fixedly, but removably attached to the slider member 78 at location 59. The proximal end 57 of the sheath 56 is fixedly, but removably connected to the lever frame 74.

The tool 36 is inserted into the working channel by the user, and the proximal ends 57, 58 of the sheath 56 and shaft section 54 are connected to the lever frame 74 and the slider member 78, respectively. FIG. 4A shows the tool actuator 72 at an actuated position which corresponds to the basket section 52 extending past the front end of the sheath 56 as shown in FIGS. 2 and 3A. FIG. 4B shows the tool actuator 72 at a home position which corresponds to the basket section 52 being located inside the front end of the sheath 56. As can be seen by reviewing FIGS. 4A and 4B, the slide member 78 is able to move on the tool actuator frame 74' to move the shaft section (control wire) 54 relative to the sheath 56, thus covering and uncovering the basket section 52 based upon the location of the slide member 78 on the tool actuator frame 74'. In one type of alternate embodiment, as discussed below with respect to the example of FIGS. 5A-5B, the tool actuator 72 may be configured to move the sheath 56 relative to the shaft section (control wire) 54.

Figure 5A:
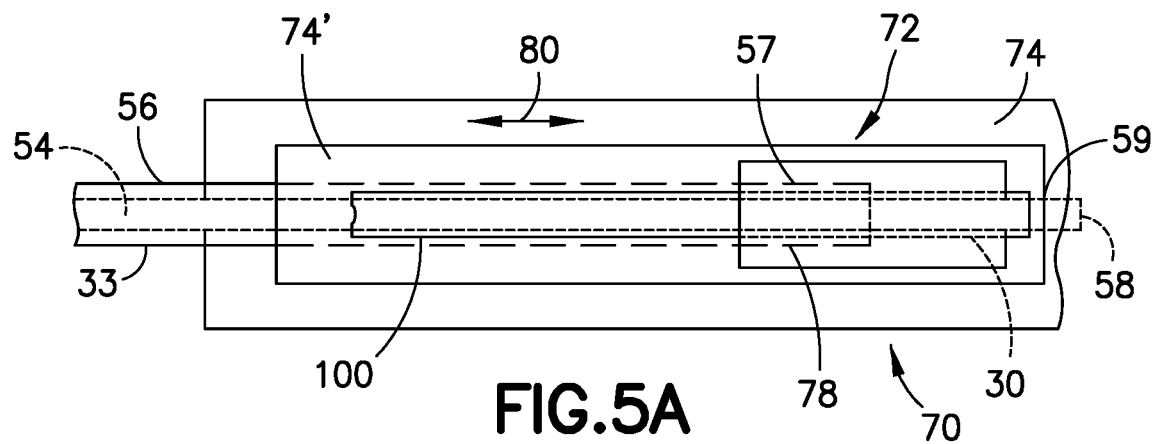
FIG. 5A is a plan view of a control of the endoscopic device shown in FIG. 2 with the slider/actuation mechanism in a first position.
Figure 5B:
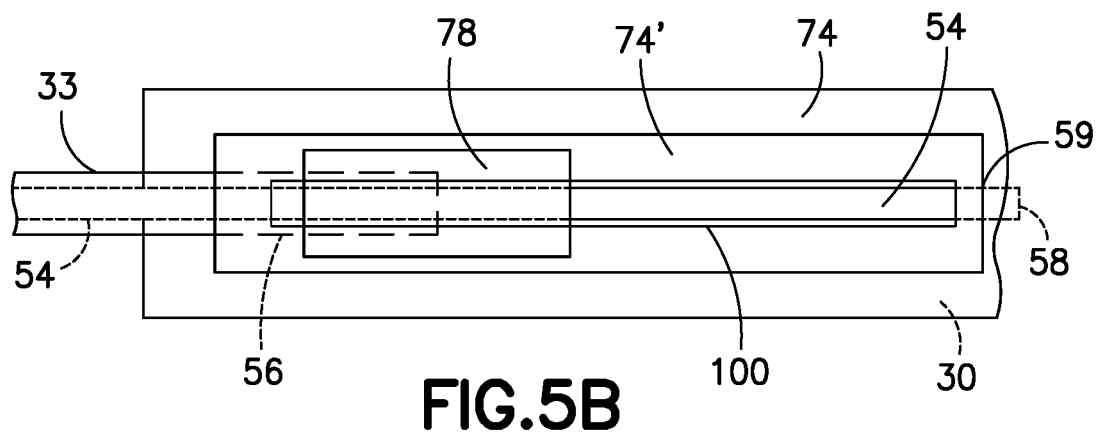
FIG. 5B is a plan view as in FIG. 5A with the slider/actuation mechanism in a second position.

Referring also to FIGS. 5A-5B an alternate example is shown. In this example the lever 30 is also both a deflection control member 70 for the actuator 28 and a tool actuator 72 for the tool 36. A frame 74 of the lever 30 is connected to the actuator 28 to be able to rotate the actuator 28 as the lever 30 is rotated forward and backward as indicated by arrow 76 in FIG. 7. The tool actuator 72 comprises a slider member 78 which is movably mounted on a slit 100 of a tool actuator frame 74' to be able to slide laterally as indicated by arrow 80. The proximal end 58 of the shaft section 54 is fixedly, but removably attached to the lever frame 74 at location 59. The proximal end 57 of the sheath 56 is fixedly, but removably connected to the slider member 78.

The tool 36 is inserted into the working channel by the user, and the proximal ends 57, 58 of the sheath 56 and shaft section 54 are connected to the slider member 78 and the lever frame 74, respectively. FIG. 5A shows the tool actuator 72 at an actuated position which corresponds to the sheath 56 being retracted on the basket device 50 such that the basket section 52 extends past the front end of the sheath 56 as shown in FIGS. 2 and 3A. FIG. 5B shows the tool actuator at a home position which corresponds to the basket section 52 being located inside the front end of the sheath 56. As can be seen by reviewing FIGS. 5A and 5B, the slide member 78 is able to move on the tool actuator frame 74' to move the sheath 56 relative to the basket device 50, thus covering and uncovering the basket section 52 based upon the location of the slide member 78 on the tool actuator frame 74'.

Figure 7:
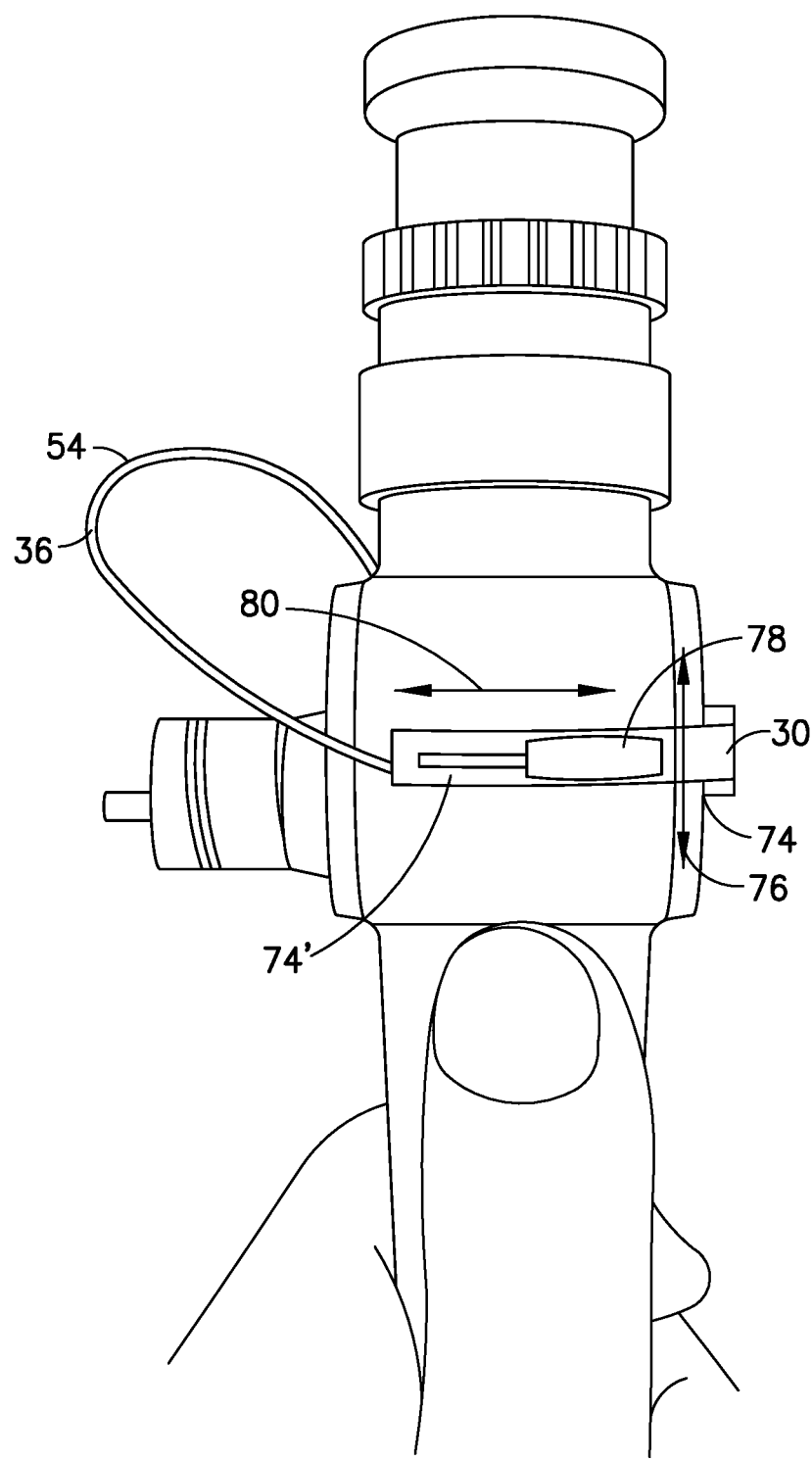
FIG. 7 is a plan view of the control of the endoscopic device being located on the deflection control of the endoscope.
Figure 8:
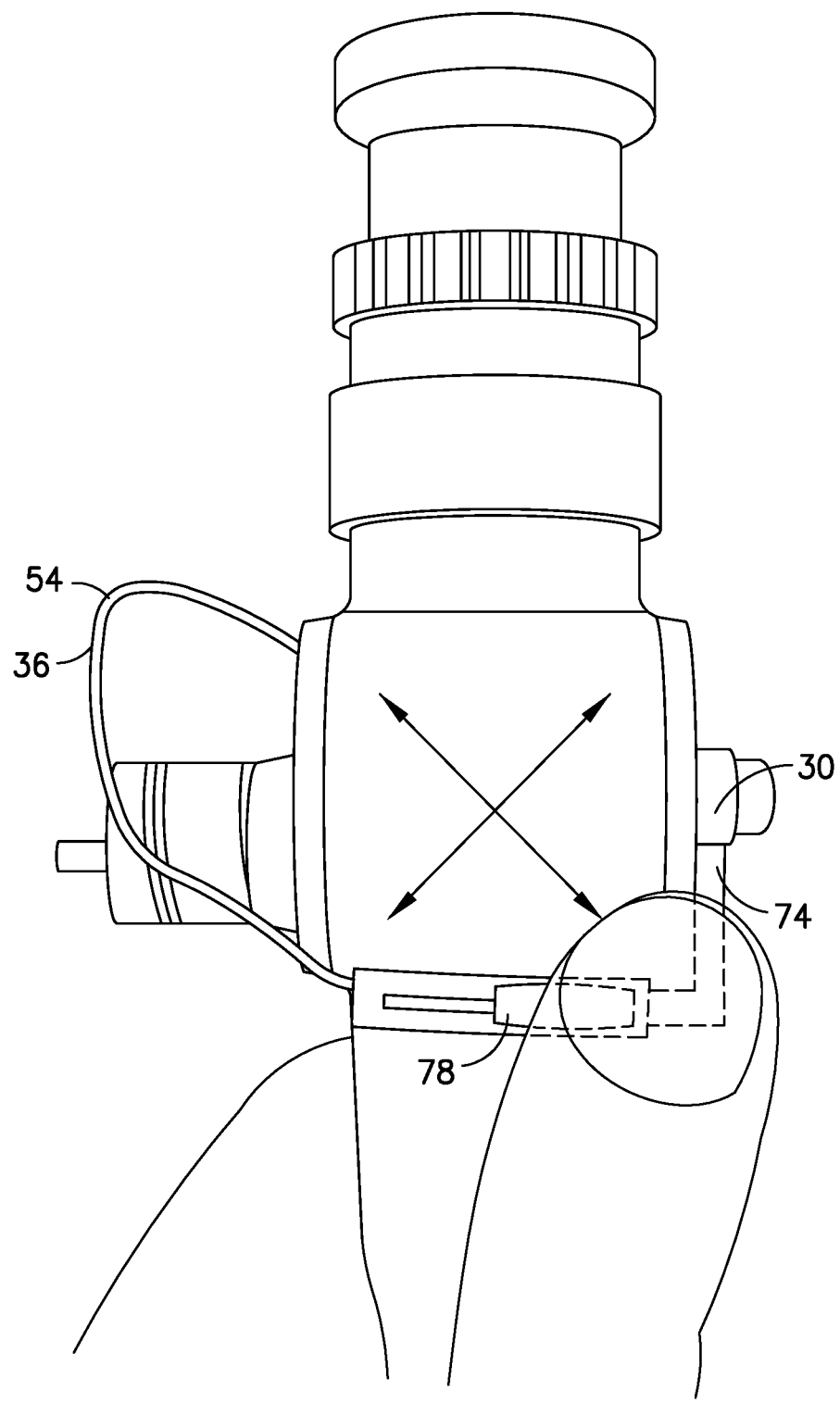
FIG. 8 is a plan view as in FIG. 7 illustrating movement of the slider/actuation mechanism on the endoscope.

As seen in FIGS. 7-8, tool 36 extends around the outside of the control section 12. The tool 36 is slidably coupled to the working channel 24 and/or the port 60 by friction or coupling mechanism. The user may manually move the tool 36 into and out of the port 60 to extend and retract the front end of the tool 36 relative to the distal end of the shaft 14. In the example shown in FIG. 8, the scope tip is deflected up (lever down) and the basket is not yet deployed out of the sheath (thumb slider to the right). The physician may control both, the scope deflection and basket activation with his/her single thumb.

Figure 9:
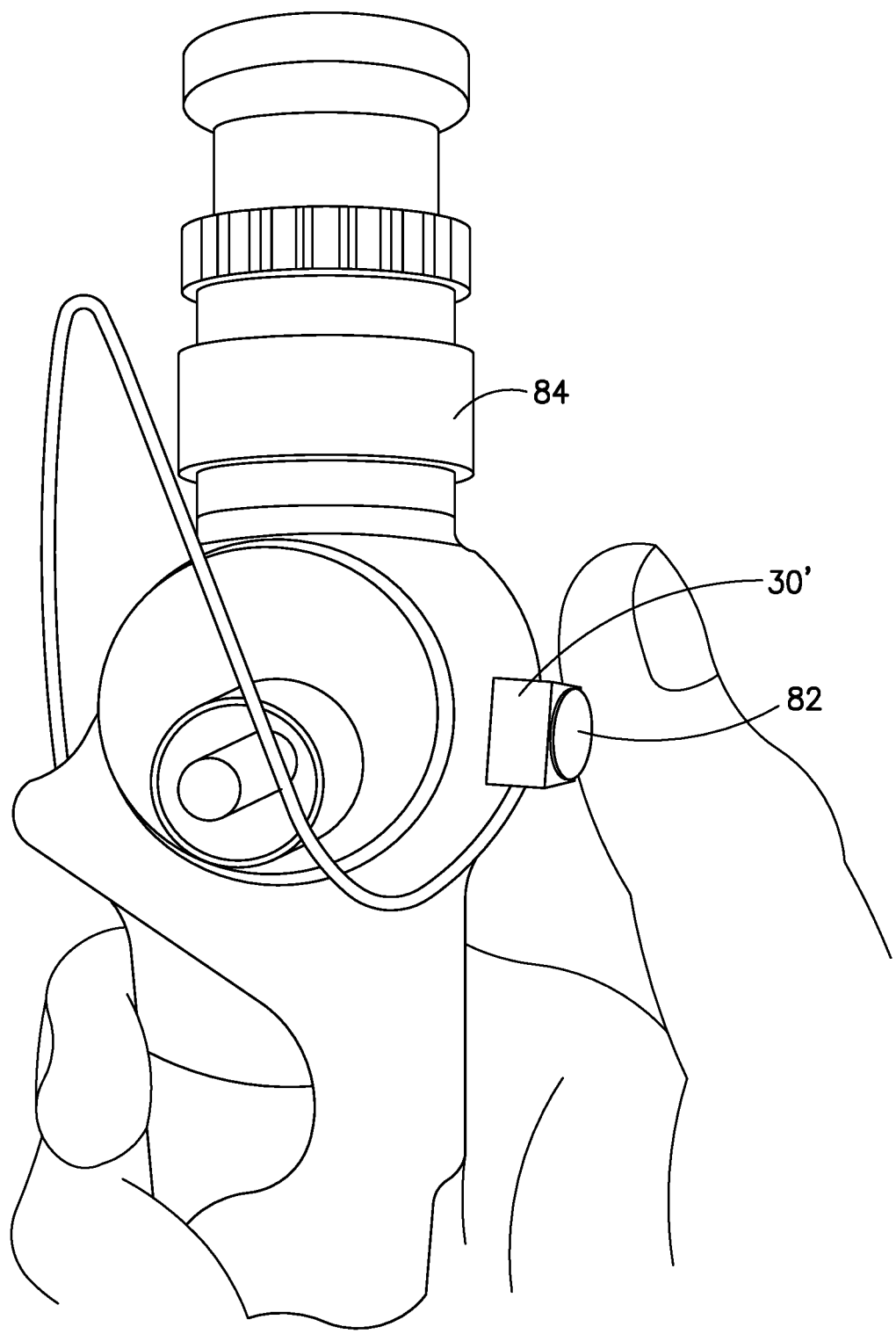
FIG. 9 is a perspective view of the endoscope with a slide-on control.
Figure 10:
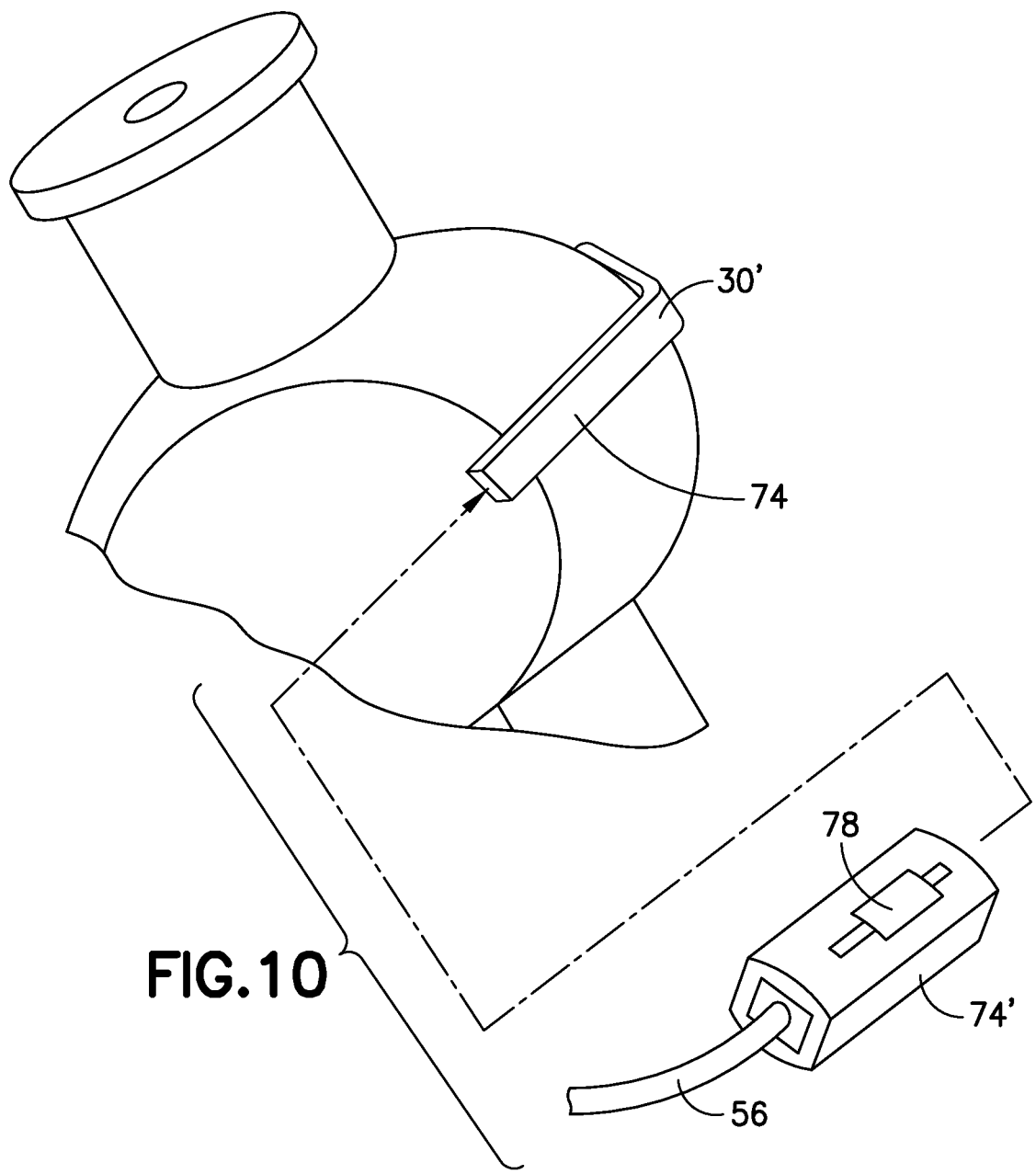
FIG. 10 is an illustration indicating the endoscopic device control of FIG. 9 being removably connected to a deflection control of the endoscope.

As illustrated by FIGS. 9 and 10, this concept could also be designed as an add-on 82 to an existing endoscope 84. In this case, the basket activation add-on would slide over an existing conventional (or modified) scope lever 30'. Tool actuator frame 74' may be slid onto the cantilevered lever frame 74 of the lever 30'.

Figure 3B:
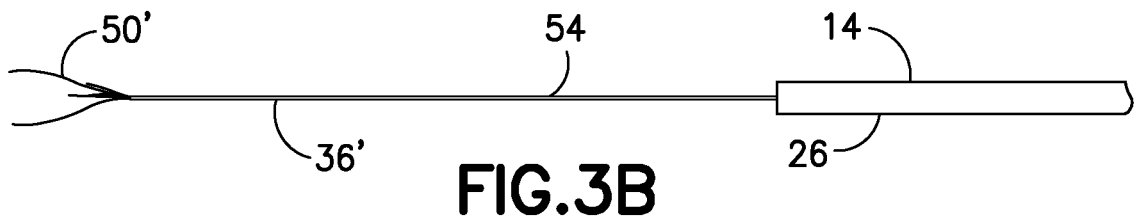
FIG. 3B is a side view of an alternate embodiment of an endoscopic tool.

Referring also to FIG. 3B, in an alternate example, the tool may not be a Surgeon Controlled Basket Device (SCBD). In this example the tool 36' has a tip of the device which is a grasper, or may be any other form of stone retrieval device. In this example the tool 36' has a working head 50' and a shaft 54. The tool 36' would be actuated by the tool actuator 72, where the shaft 54 is connected to the tool actuator 72.

Features as described herein may be used for a surgeon controlled basket and scope design; the surgeon being able to use one hand to hold the insertion portion and the other hand to hold the handle of the endoscope and control the scope deflection. Conventionally, there is no hand free to control the basket/ET-device at the same time. For this reason, assistance is required to hold the basket handle and to deploy/retrieve the basket. Features as described herein allow a physician to control both, the scope deflection and the basket deployment with one thumb and without another person's help. Features as described herein may be used to provide a combined basket thumb slider and scope lever into one actuation mechanism; the lever 30 or 30'. Thus, the lever for the scope deflection of the distal end may have an integrated thumb slider for the basket actuation.

Features as described herein may relate to an endoscope, lithotripsy device, kidney stone retaining basket, grasper, clip-on basket control device, and/or rotatable detachable stone basket. Urology lithotripsy and surgery processes require using grasping or biopsy forceps and a retaining basket which operates by a control wire that extends through a sheath. Most existing instruments have a slider which moves along a handle, separate from the handle of the endoscope, operating the device with a sliding motion and locking mechanism. Existing devices are designed such that more than one person is required to effectively conduct a stone retrieval procedure. This is because existing devices each require one or two hands to operate, and devices must be coordinated simultaneously to properly perform the procedure. For example, one or two hands are required to perform each of the following functions, manipulate and control:
   the endoscope;
   the irrigation flow rate;
   accessories such as
      guidewires,
      catheters,
      access sheaths,
      balloon dilators,
      graspers,
      stents,
      baskets.

For this reason, the primary surgeon is generally supported by a medical assistant or nurse. Typically the attending surgeon switches between one and two-handed control of the endoscope and uses the free hand to intermittently perform the other activities listed above, and is therefore unable to effectively control the stone retrieval device at the same time. The process of capturing kidney stone fragments in a basket may involve:
   locating the fragments with the endoscope,
   properly positioning the basket and sheath,
   carefully deploying (opening) the basket such that it does not move the fragments away so that they need to be located again,
   rotating the open basket such that the basket wires surround the stone fragments,
   carefully retracting (closing) the basket such that the basket wires grasp the stone fragments,
   carefully removing both the endoscope and the basket from the patient ensuring that the fragments do not get stuck in the access sheath, or patient's anatomy,
   and finally releasing the stone fragments from the basket or graspers outside of the patient's body.

One of the important steps described above is to properly rotate the basket, for consistent capturing of the stone fragments, without accidentally moving the fragments around or causing them to drop out of the retrieval device if possible. In the process of "fishing" and capturing the kidney stone's fragments they are very often lost when the basket closes. This happens because, conventionally, the basket is moving back and the sheath is fixed. Additionally, sometimes stone fragments start to obscure the physician's vision while breaking up a larger stone, so instruments are switched in and out of the working channel to intermittently break up stones and retrieve fragments. This requires that the stone retrieval device be capable of quickly being exchanged with a lithotripsy or other accessory.

Features as described herein were designed for one hand control of the endoscope and stone retrieval device. The surgeon can hold both the endoscope and the basket control device using only one hand. The second hand can be used for additional manipulation, changing and adjusting accessories and irrigation using syringe or liquid container adapter valve. Basically it permits the surgeon to perform the entire procedure without additional specialists' support. The device allows the sheath to move with a fixed basket, or moves both the sheath and basket simultaneously while opening and closing. This feature reduces the possibility of losing fragments of stones during the basket closing process. It also supports the rotation of the stone retrieval device with the same hand, quick removal and detachment from the endoscope, and quick insertion and reattachment to the endoscope.

Figure 11:
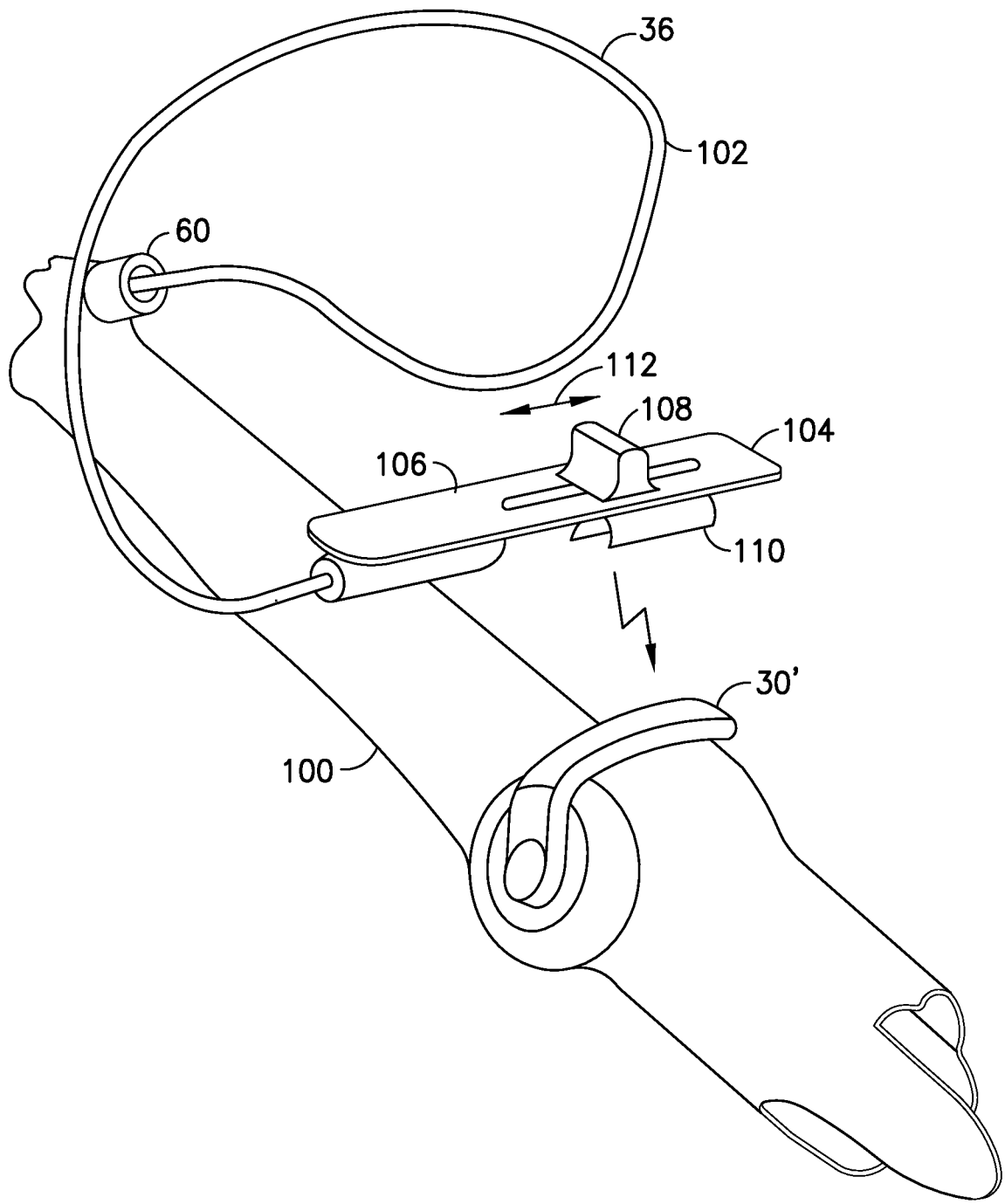
FIG. 11 is an alternate embodiment of the control shown in FIG. 10 and a portion of the endoscope.

Referring also to FIG. 11, a portion of a control section 12 of an endoscope 100 is shown with another example embodiment. The endoscope 100 includes a working port entrance 60 and a deflection control lever 30'. The endoscopic device 102 comprises the endoscopic tool 36 and the control 104. The endoscopic tool 36 is the same as described above with the sheath 56 and the basket device 50. The control 104 comprises a housing 106 and a slider 108, or actuation mechanism. The housing 106 includes a connector 110 which is sized and shaped to snap on to the deflection control lever 30'. The sheath and the basket device form first and second members which the slider 108 may be attached to. The slider is longitudinally mounted on the housing 106 to slide back and forth as indicated by arrow 112 to longitudinally move the sheath and basket device relative to each other between an extended position and a retracted position.

Figure 12:
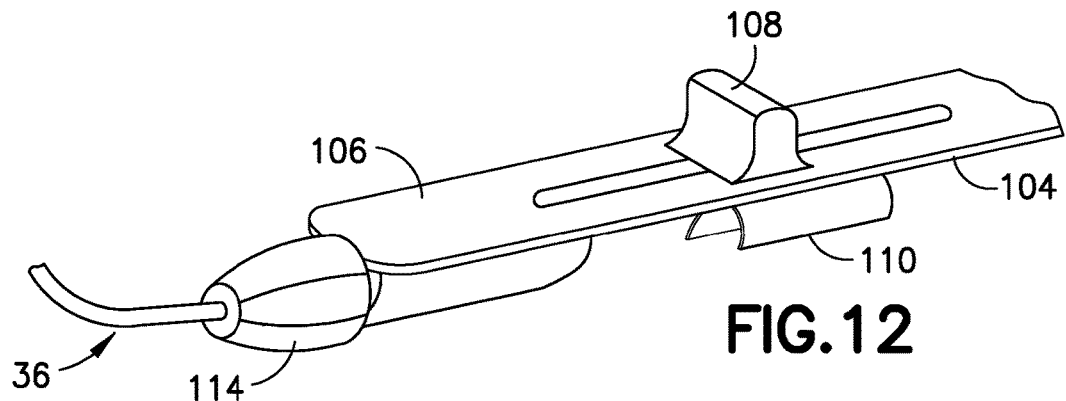
FIG. 12 is a perspective view of an alternate embodiment of the control shown in FIG. 11.

Referring also to FIG. 12, an example embodiment similar to that of FIG. 11 is shown. However, in this example a rotating connector 114 is added as a connection of the proximal end of the endoscopic device 36 to the control 104. FIG. 12 is a view of a rotating version of the surgeon controlled stone retrieval device (SCRD) with a clip-on or slide-on coupling feature to the endoscope deflection lever. In the example, sliding the lever 108 to the left would deploy the stone retrieval device, and sliding the lever 108 to the right could retract the stone retrieval device. Since the entire SCRD assembly is rigidly, but removably coupled to the endoscope deflection lever 30', pushing the control 104 up or pulling the control 104 down also moves the endoscope deflection lever 30 up and down respectively. The same thumb used to both deflect the endoscope at lever 30' and deploy or retract the stone retrieval device at slider 108 can also be used to rotate the endoscope 100 while in the patient. Deploying or opening the stone retrieval device means exposing the stone retrieval portion 52 of the retrieval tool 36. Retracting or closing the stone retrieval tool 36 means causing the retrieval portion 52 of the retrieval tool 36 to retract back into its sheath 56, or to "capture" targeted stone fragments. Neither of these terms are meant to restrict the mechanism of relative motion between the sheath and the retrieval portion of the retrieval device. As further understood from the examples described below, the retrieval portion may be moved relative to a stationary sheath, the sheath may be moved relative to a stationary basket, or both the retrieval portion and the sheath may be moved simultaneously relative to each other.

Figure 13:
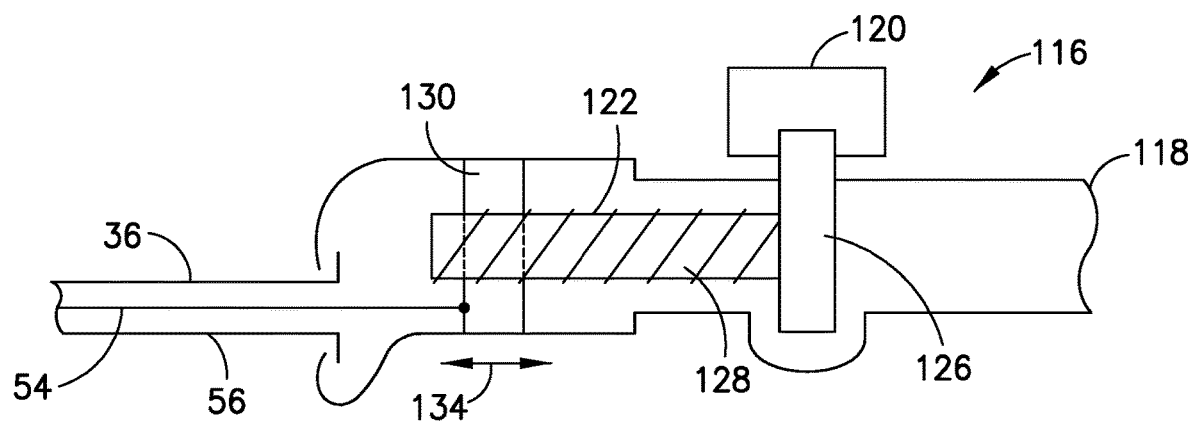
FIG. 13 is a schematic illustration of another example embodiment of the endoscopic device control.
Figure 14:
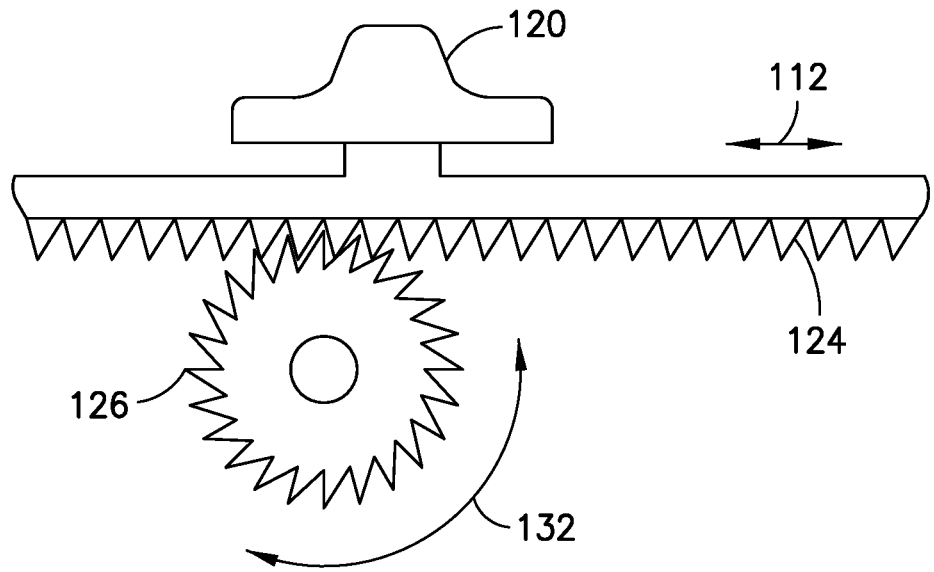
FIG. 14 is schematic illustration of some of the components of the control shown in FIG. 13.

Referring also to FIGS. 13-14, an alternate example embodiment of the control of the endoscopic device is shown. In this example the control 116 comprises a housing 118, a slider 120 (actuation mechanism) and a transmission 122. The housing 118 may have a connector such as the connector 110 or the connector 74' for example. The transmission 122 comprises a rack section 124 on the slider 120, a pinion section 126 connected to a worm gear 128, and a worm gear follower 130. The proximal end of the shaft section 54 is connected to the worm gear follower 130. As the slider 120 is longitudinally moved on the housing 118 in directions 112, the rack section 124 causes the pinion section 126 to rotate as indicated by arrow 132. Rotation of the pinion section 126 causes the worm gear 128 to axially rotate which, in turn, causes the follower 130 to longitudinally move as indicated by arrow 134. When the follower 130 moves, the shaft section 54 of the basket device is longitudinally moved relative to the sheath 56. In an alternate example, any suitable transmission may be provided.

Figure 15:
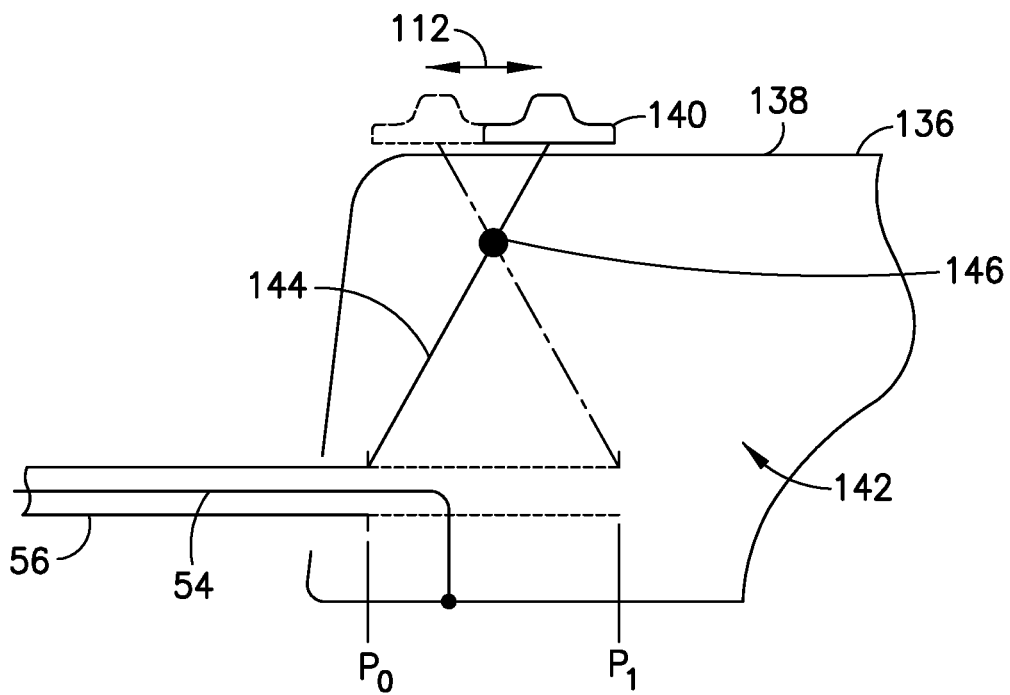
FIG. 15 is a schematic illustration of another example embodiment of the endoscopic device control.

Referring also to FIG. 15, another alternate example embodiment is shown. In this example the endoscopic device comprises the endoscopic tool 36 and a control 136. The control 136 includes a housing 138, a slider 140 (actuation mechanism) and a transmission 142. The housing 138 may have a connector such as the connector 110 or the connector 74' for example. The transmission 142 includes a pivot arm 144 connected to the housing 138 by a pivotable connection 146. Opposite ends of the pivot arm 144 are connected to the slider 140 and the proximal end of the sheath 56. The proximal end of the shaft section 56 is fixed to the housing 138. As the slider 140 is longitudinally moved as indicated by arrow 112, the proximal end of the sheath 56 is longitudinally moved relative to the shaft section 54 to thereby move the endoscopic tool between its extended configuration and its retracted configuration. When the proximal end of the sheath 56 is at $P_0$, the shaft is located over the basket section. When the proximal end of the sheath 56 is at $P_1$, the basket section is exposed to an enlarged position in front of the distal end of the sheath.

Figure 16:
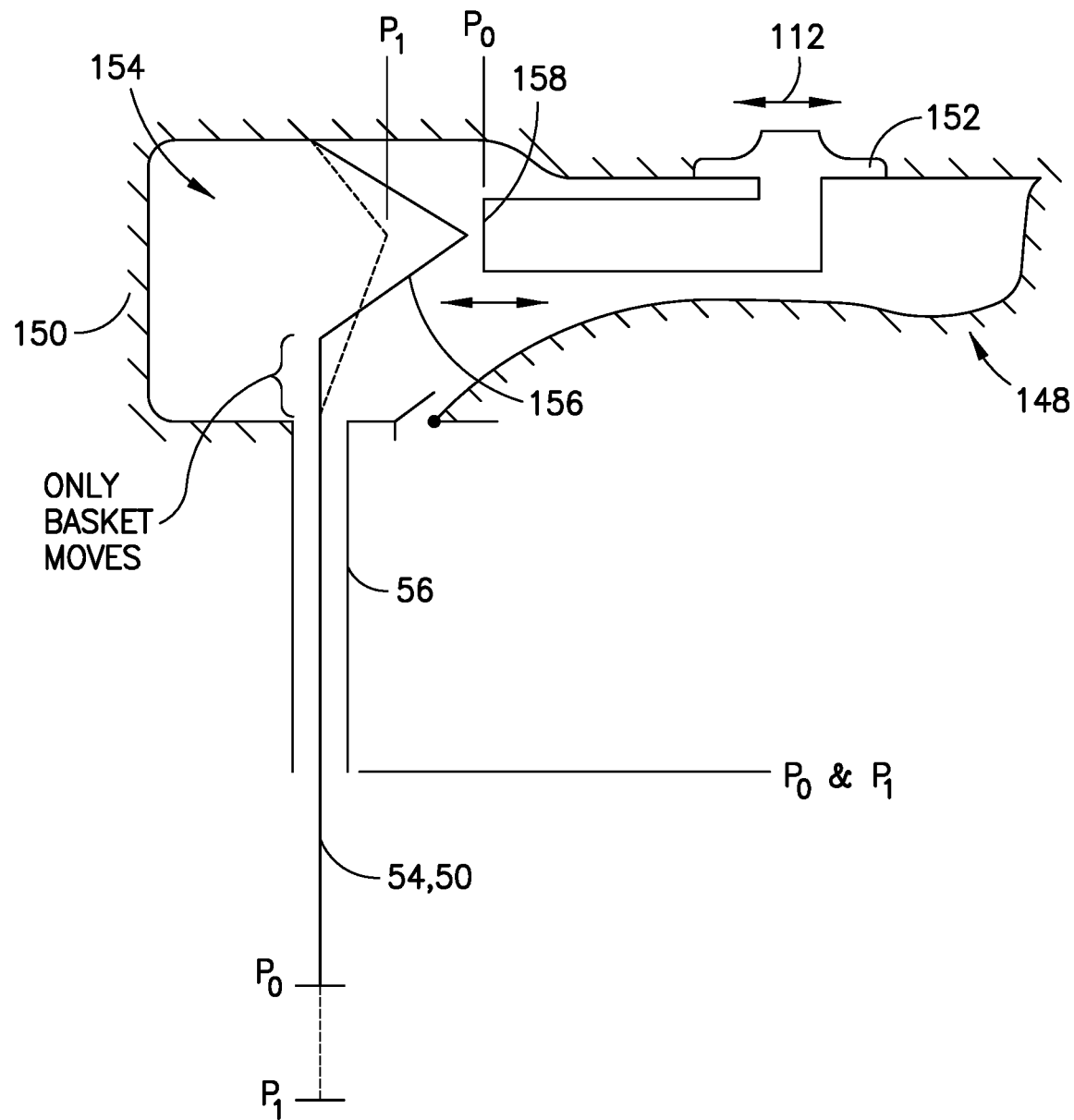
FIG. 16 is a schematic illustration of another example embodiment of the endoscopic device control.

Referring also to FIG. 16, another alternate example embodiment is shown. In this example the endoscopic device comprises the endoscopic tool 36 and a control 148. The control 148 includes a housing 150, a slider 152 (actuation mechanism) and a transmission 154. The housing 150 may have a connector such as the connector 110 or the connector 74' for example. The proximal end of the sheath 56 is stationarily connected to the housing 150. The transmission 154 includes a "V" spring 156. One end of the V spring 156 is stationarily connected to the housing and the other end of the V spring 156 is connected to the shaft section 54 of the endoscopic tool 36. FIG. 16 shows the V spring, shaft section 54 and slider 152 at a home position $P_0$. When the proximal end of the basket device 50 is at $P_0$, the shaft is located over the basket section. When the slider 152 is moved, the end 158 of the slider can deflect the V spring 156 to position $P_1$ which moves the basket device 50 to position $P_1$. When the proximal end of the basket device 50 is at $P_1$, the basket section is exposed to an enlarged position in front of the distal end of the sheath.

Figure 17:
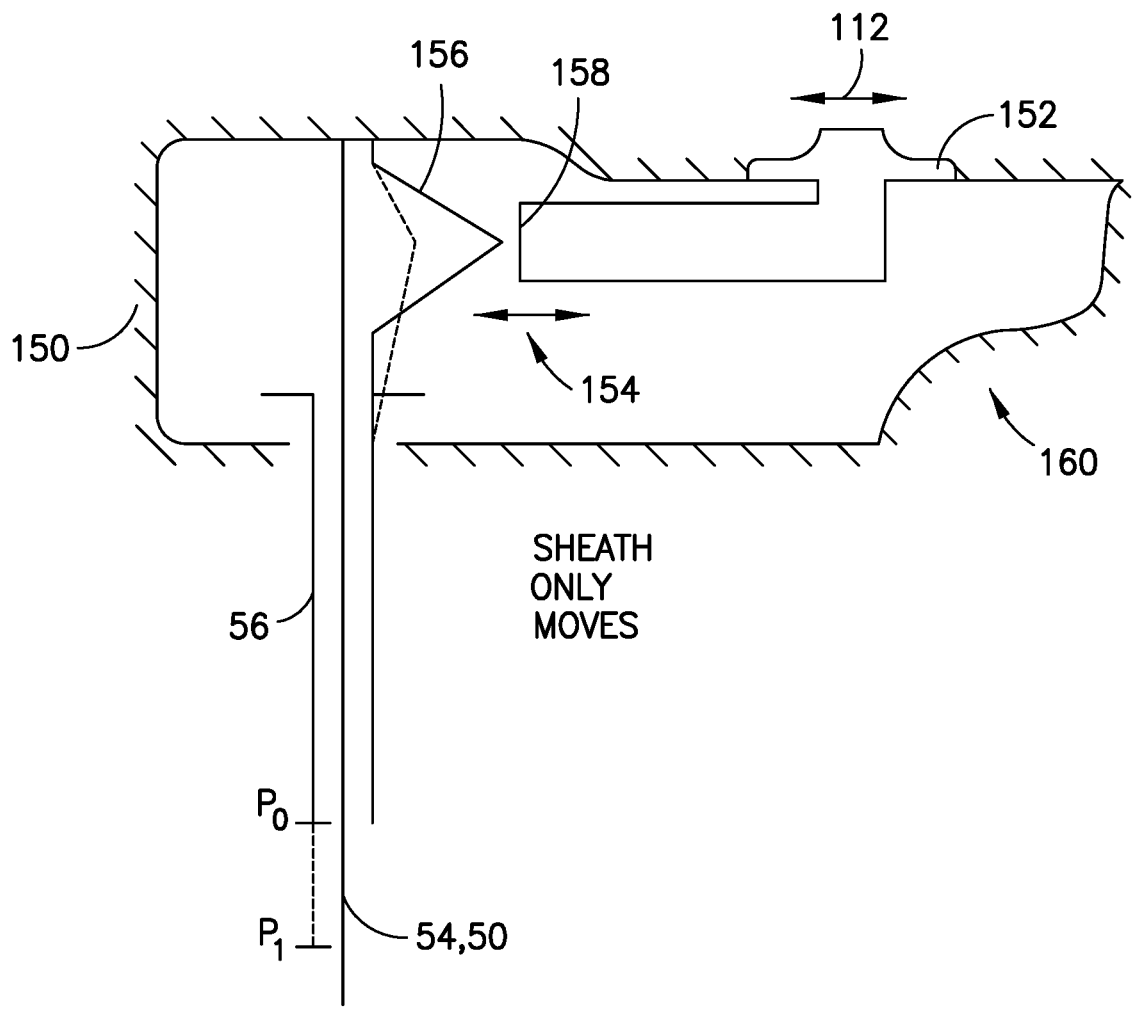
FIG. 17 is a schematic illustration of another example embodiment of the endoscopic device control.
Figure 18:
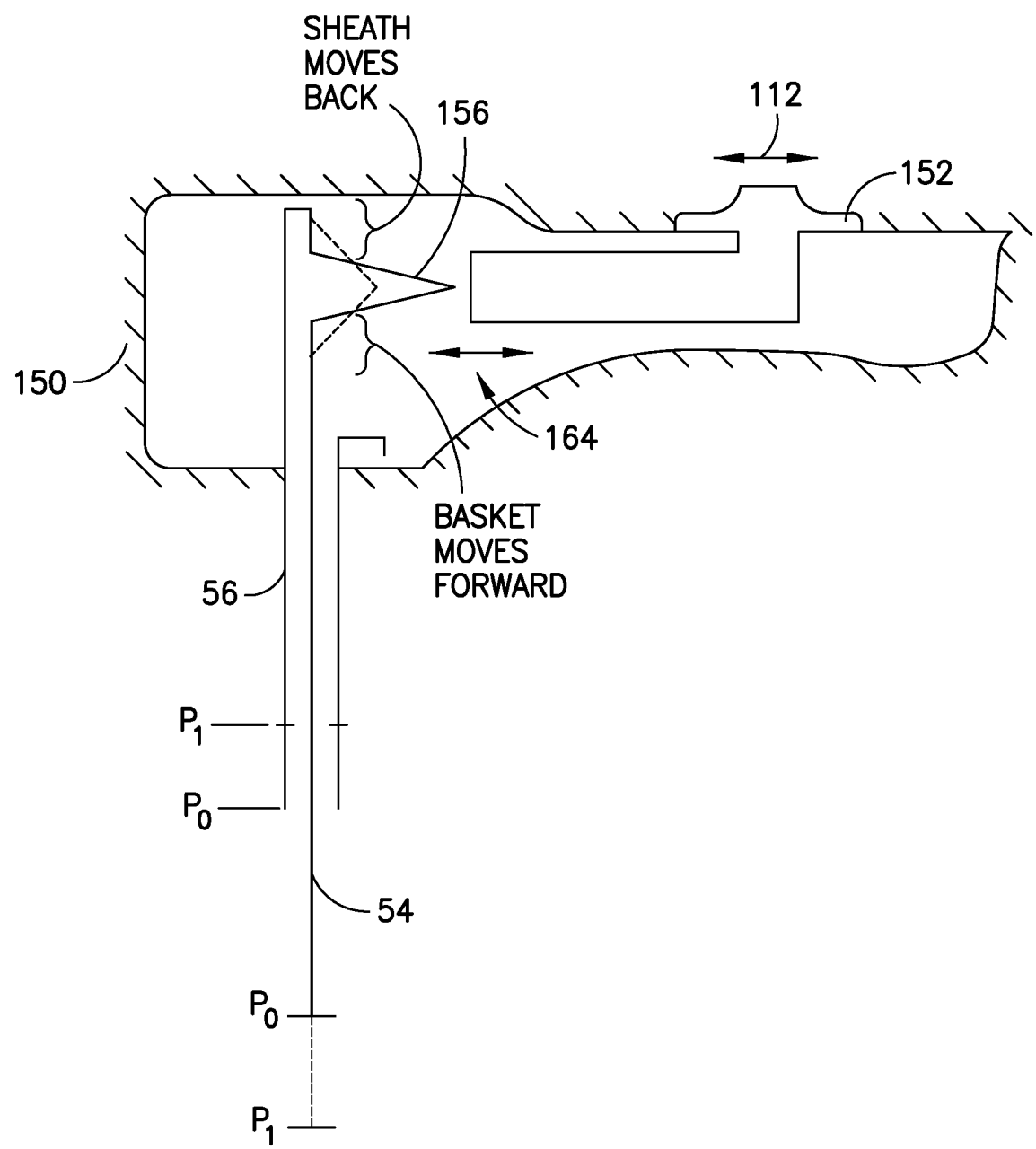
FIG. 18 is a schematic illustration of another example embodiment of the endoscopic device control.

Referring also to FIG. 17, another alternate example embodiment is shown. In this example the endoscopic device comprises the endoscopic tool 36 and a control 160. The control 160 includes a housing 150, a slider 152 and a transmission 154. The housing 150 may have a connector such as the connector 110 or the connector 74' for example. The proximal end of the shaft section 54 is stationarily connected to the housing 150. The transmission 154 includes a "V" spring 156. One end of the V spring 156 is stationarily connected to the housing and the other end of the V spring 156 is connected to the sheath 56 of the endoscopic tool 36. FIG. 17 shows the V spring, shaft section 54 and slider 152 at position $P_0$. When the proximal end of the sheath 56 is at $P_0$, the basket section is exposed to an enlarged position in front of the distal end of the sheath. When the slider 152 is moved, the end 158 of the slider can deflect the V spring 156 to move the sheath 56 to position $P_1$. At $P_1$, the shaft is located over the basket section. In the example embodiment of FIG. 17 the sheath 56 is longitudinally moved relative to the basket device 50, and in the example embodiment of FIG. 16 the basket device 50 is longitudinally moved relative to the sheath 56. In FIG. 18, both the basket device 50 and the sheath 56 are longitudinally moved relative to the housing 150.

As seen in FIG. 18, in this example the endoscopic device comprises the endoscopic tool 36 and a control 162. The control 162 includes a housing 150, a slider 152 and a transmission 164. The housing 150 may have a connector such as the connector 110 or the connector 74' for example. The transmission 164 includes a "V" spring 156. The proximal end of the shaft section 54 is connected to the V spring 156. The proximal end of the sheath 56 is connected to the other end of the V spring 156. As the slider 152 is moved to straighten the V spring 156, the basket device 50 is moved forward and the sheath is moved backward from $P_0$ to $P_1$.

It is contemplated that additional alternative embodiments may be used for actuation of the sheath and the basket device. Such a device may be removably attached to an endoscope lever such that control of the endoscope tip deflection as well as control of movement of the basket and sheath might be possible with a single finger of a user. For example, control cables for controlling basket device and sheath movement may be connected directly to the actuation mechanism. It is contemplated that the actuation mechanism may be other than a thumb slider. By way of example, the actuation mechanism may be a joystick control, a rotating wheel, a set of rotating wheels, a pivotable rod, a push rod, a drum pivot with control cables wrapped around it. The actuation mechanisms described may be removably attached to the control lever of the endoscope handle, for example.

Figure 19:
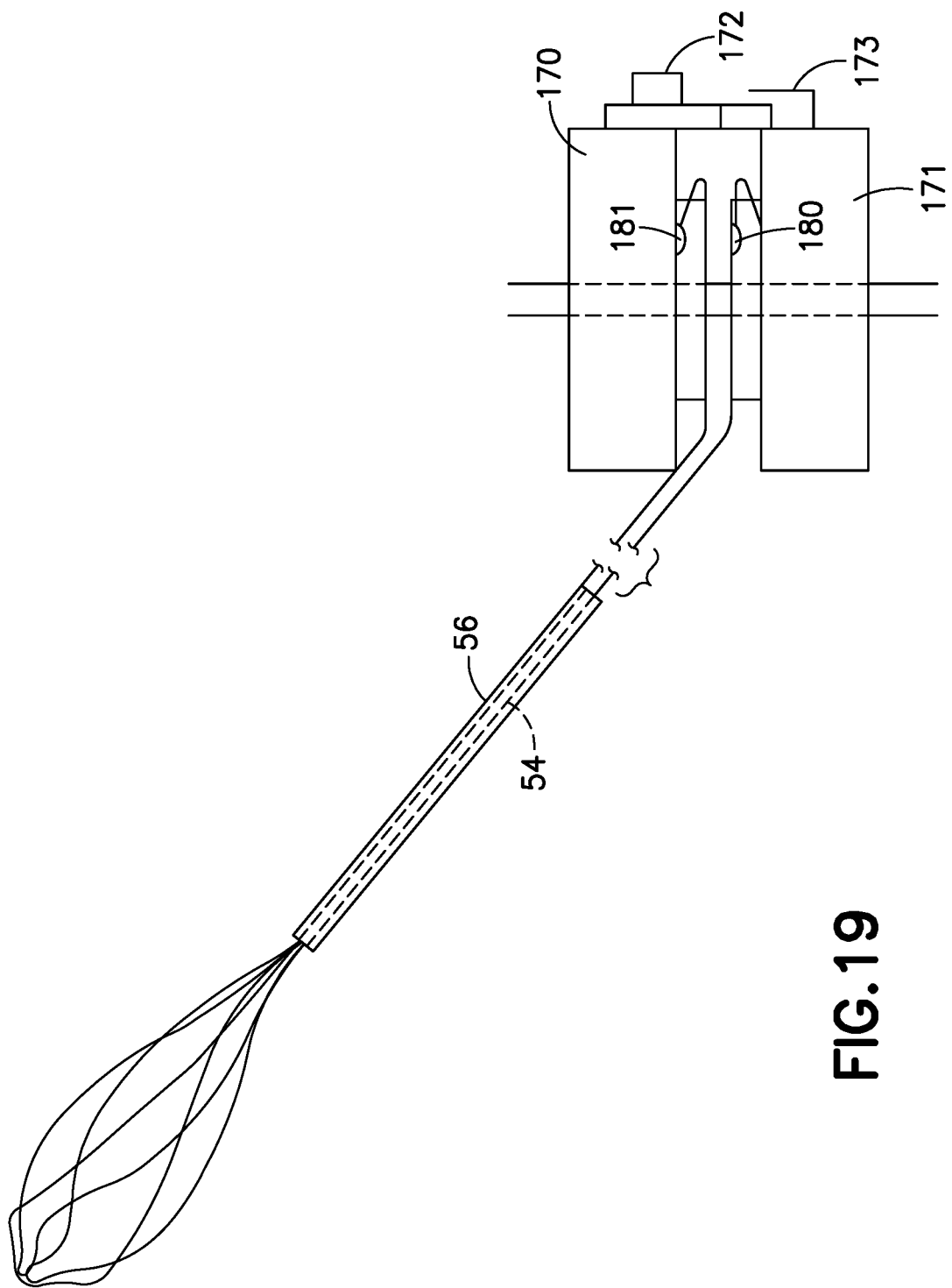
FIG. 19 is a schematic illustration of another example embodiment of the endoscopic device control.
Figure 20:
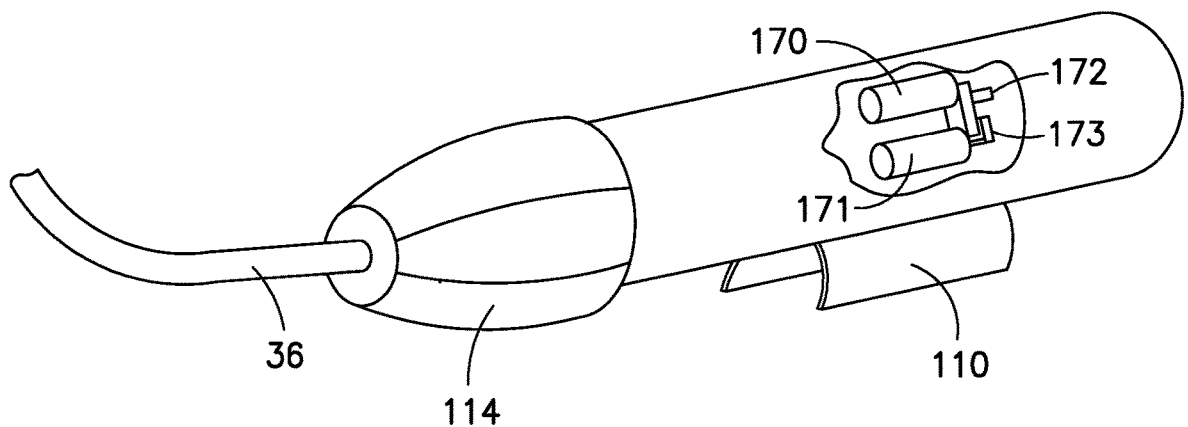
FIG. 20 is a schematic illustration of another example embodiment of the endoscopic device control.

An example embodiment is illustrated in FIG. 19 showing a set of rotating wheels 170 and 171 being used for actuating a basket 54 and sheath 56. A control cable for controlling movement of the sheath 56 may be connected to one wheel at point 181, for example, and a control cable for controlling movement of basket 54 may be connected to another wheel at a point 180. A locking mechanism may include a slider 172 which connects into a lock 73 may be provided for the two wheels 170 and 171 to allow for basket 54 and sheath 56 to be moved simultaneously when desired, providing for increased flexibility and control over the basket and sheath actuation. FIG. 20 shows an example embodiment of a set of rotating wheels for actuating a basket and sheath located on a detachable mechanism for attaching to the control lever of an endoscope, with a rotation function additionally provided for rotating the basket and sheath assembly.

Figure 21:
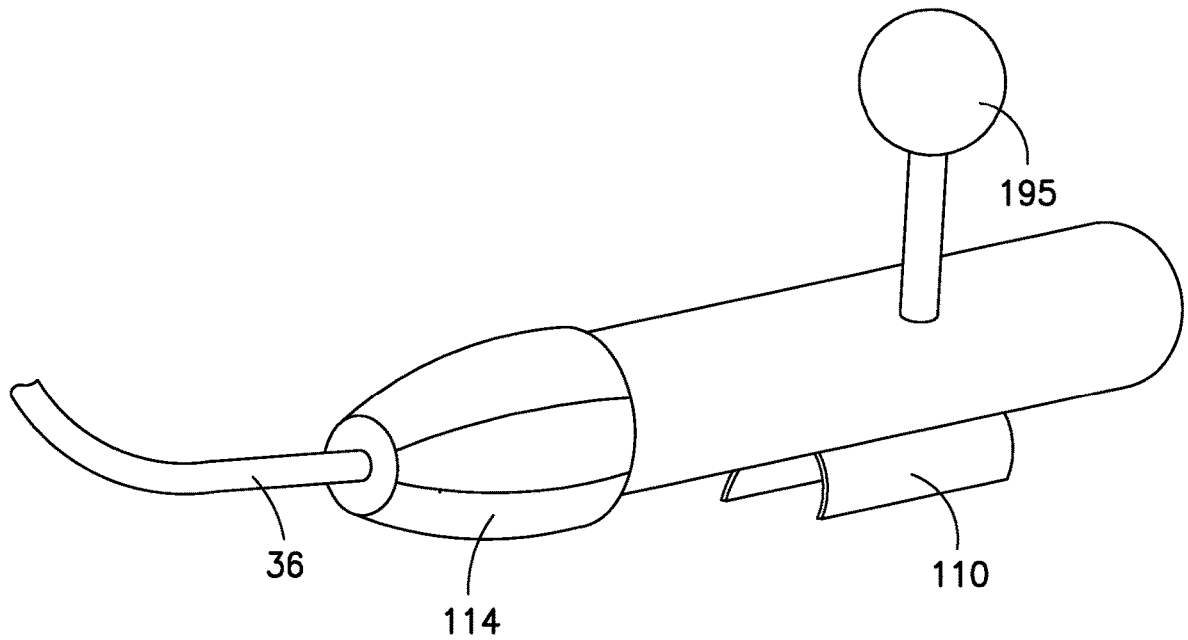
FIG. 21 is a schematic illustration of another example embodiment of the endoscopic device control.
Figure 22:
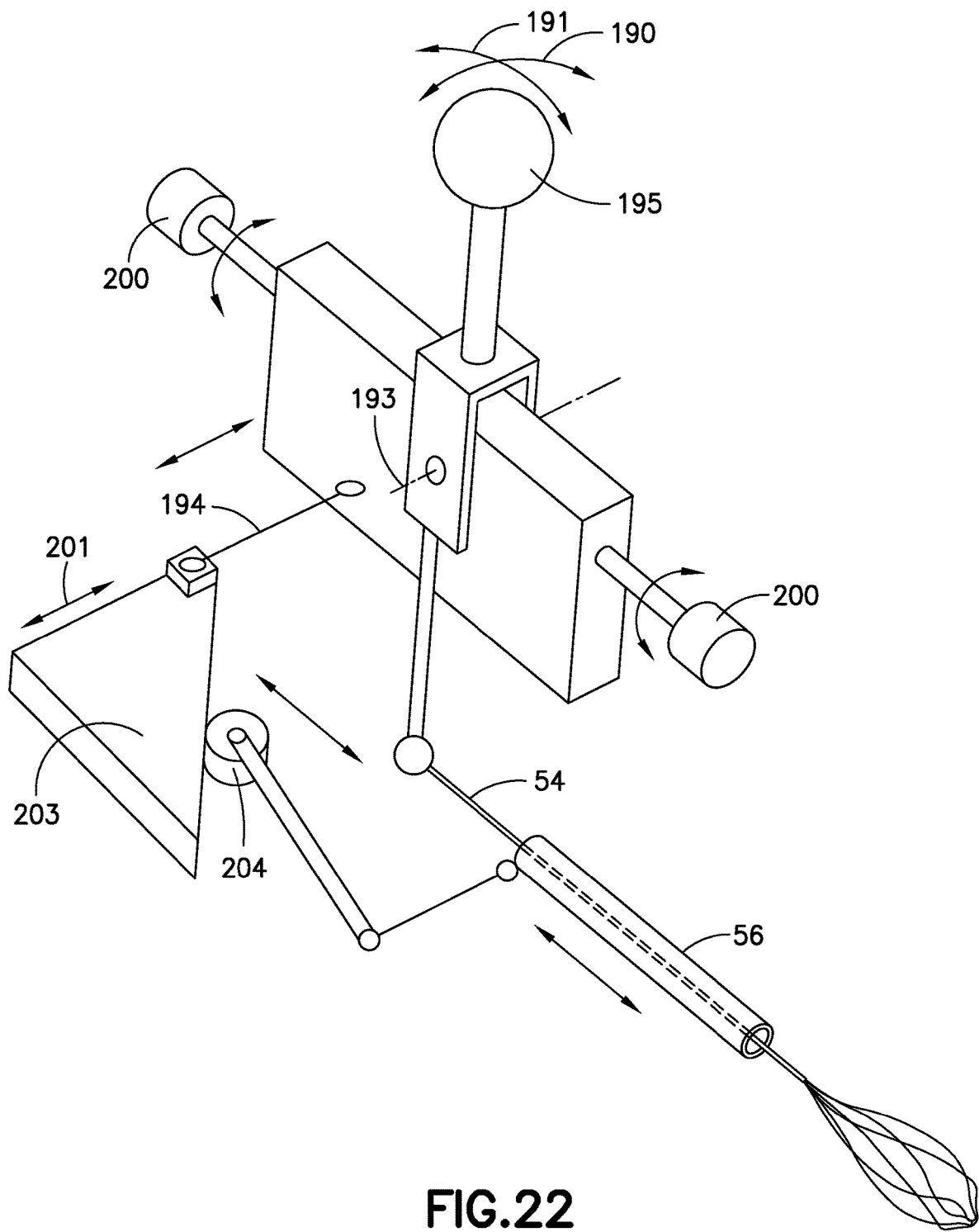
FIG. 22 is a schematic illustration of another example embodiment of the endoscopic device control.

An example embodiment is illustrated in FIG. 21 showing joystick actuation for controlling actuation of a basket and a sheath. Joystick 195 can be moved in a first direction, 190, or a second direction 191. Moving joystick 195 in a first direction 190 causes a rotation about a pivot point 193 causing movement of basket 54. Moving joystick 195 in a second direction 191 causes movement about a second pivot point and movement of a block 203 via linkage 194. This movement in turn causes sliding of a roller 204 which actuates movement of sheath 56. Moving a joystick controller from left to right, for example, might control movement of the basket and moving the joystick up and down might control movement of the sheath. FIG. 22 shows an example embodiment of a joystick mechanism for actuating a basket and sheath located on a detachable mechanism for attaching to the control lever of an endoscope, with a rotation function additionally provided for rotating the basket and sheath assembly. Such a mechanism would allow for movement of the deflection of the endoscope distal end, actuation of a basket and actuation of a sheath with a single finger of a user.

Figure 23:
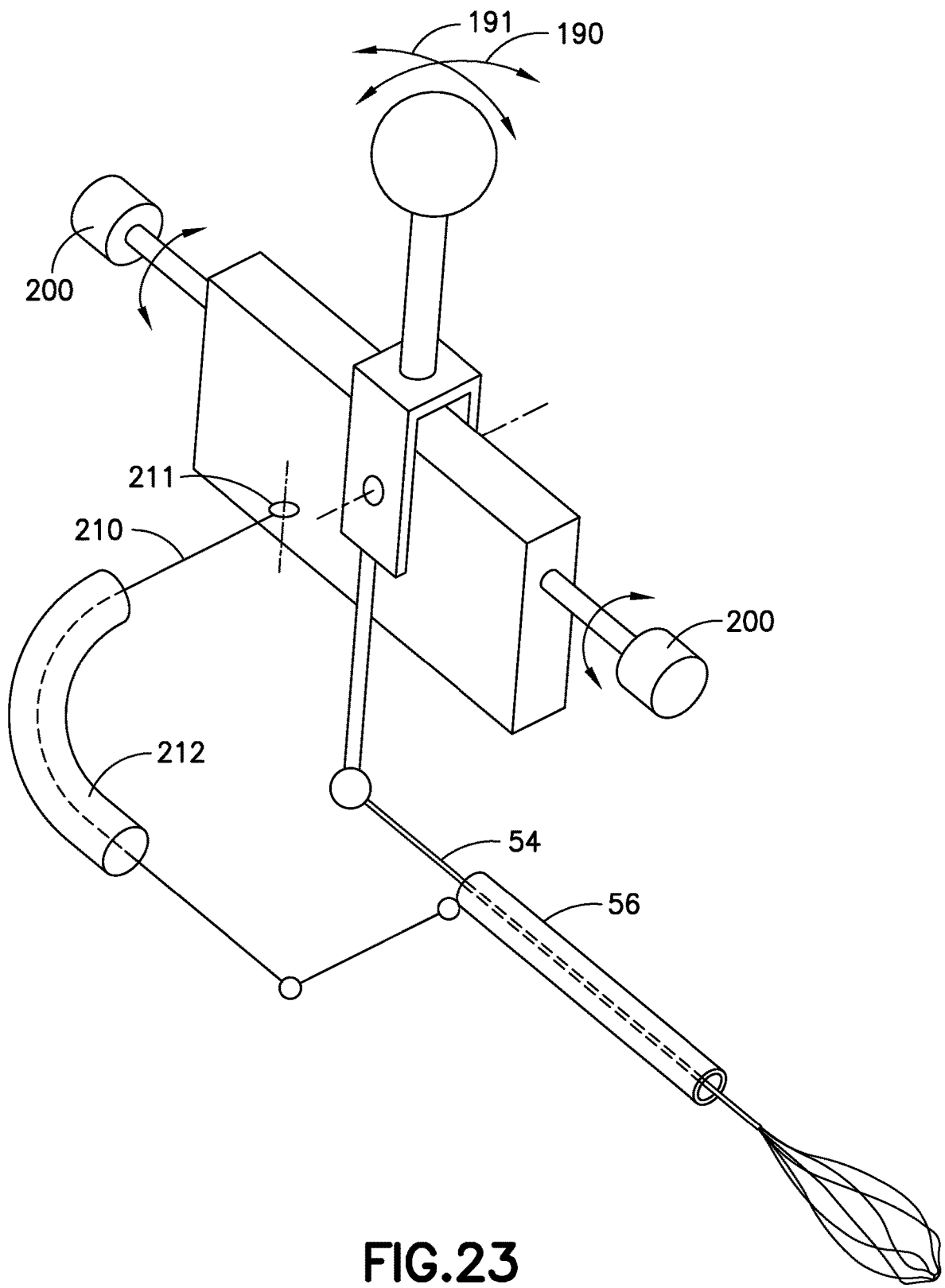
FIG. 23 is a schematic illustration of another example embodiment of the endoscope device control.

FIG. 23 shows an example embodiment of an alternative joystick mechanism for actuating a basket and sheath located on a detachable mechanism for attaching to the control lever of an endoscope, with a rotation function provided for rotating the basket and sheath assembly. Joystick 195 can be moved in a first direction, 190, or a second direction 191. In this embodiment, a stiff flexible cable 210 would connect to the pivot block 211 through a pivot joint 212 and be routed through a bended conduit. The conduit is bent through 90 degrees. This would translate the side-to-side motion of the pivot block into a linear in-out motion to actuate the sheath. Moving a joystick controller from left to right, for example, might control movement of the basket and moving the joystick up and down might control movement of the sheath.

It is additionally contemplated that a robotic actuation mechanism may be used for controlling movement of the basket and sheath or for controlling movement of a basket, a sheath, and deflection of an endoscope distal end. For example, electrical motors may be utilized to drive motion when actuation levers, dials, or joysticks are actuated.

In one type of example embodiment, a medical apparatus comprises an endoscope comprising a bending portion and a handle portion; an endotherapy device having an effecter part and at least one control wire connected to the effecter part; a coupling portion connecting the endotherapy device to the endoscope, wherein the coupling portion is configured to extend the control wire along a surface of the handle portion; a control lever located at the handle portion and configured to linearly move in a first direction for controlling the bending section; and a slider located and configured to linearly move in a second direction on the control lever, wherein the slider includes a connecting portion configured to connect a proximal end of the control wire for controlling the effecter part.

In one type of example embodiment a medical apparatus comprises an endoscopic tool comprising first and second members longitudinally slidable relative to each other; and a control connected to a proximal end of the endoscopic tool, where the control comprises a housing and a slider, where the slider is longitudinally slidably connected to the housing, where the slider has the first member and/or the second member connected thereto, and where the housing comprises a connector configured to removably connect the housing to a control section of an endoscope.

The first member may comprise a sheath and the second member comprises basket device. A proximal end of the sheath may be connected to the slider and a proximal end of the basket device is connected to the housing. A proximal end of the basket device may be connected to the slider and a proximal end of the sheath is connected to the housing. The connector may be sized and shaped to longitudinally slide on to a deflection control lever of the control section of the endoscope. The connector may be sized and shaped to resiliently snap on to a deflection control lever of the control section of the endoscope. A connection of the first member and/or the second member to the slider may comprise a rack and pinion configuration. A connection of the first member and/or the second member to the slider may comprise a pivoting member. A connection of the first member and/or the second member to the slider may comprise a spring member. The spring member may comprise a "V" shape.

An example method may comprise inserting a distal end of an endoscopic device into a working channel of an endoscope, where the endoscopic device comprises an endoscopic tool, where the endoscopic tool comprises first and second members which are longitudinally slidable relative to each other; and removably connecting a proximal end of the endoscopic device to a control section of the endoscope, where the proximal end comprises a housing and a slider, where the slider is slidably connected to the housing, where the slider has the first member and/or the second member connected thereto, and where the housing comprises a connector which removably connects the housing to the control section of the endoscope.

The first member may comprise a sheath and the second member comprises basket device, where inserting the distal end of the endoscopic device into the working channel of the endoscope comprises inserting distal ends of the sheath and the basket device into the working channel. Removably connecting the proximal end of the endoscopic device to the control section of the endoscope may comprise longitudinally sliding the housing on to a deflection control lever of the control section of the endoscope. Removably connecting the proximal end of the endoscopic device to the control section of the endoscope may comprise resiliently snapping the housing onto to a deflection control lever of the control section of the endoscope.

An example method may comprise providing an endoscopic tool, where the endoscopic tool comprises first and second members which are longitudinally slidable relative to each other; and connecting a control to a proximal end of the endoscopic tool, where the control comprises a housing and a slider, where the slider is longitudinally slidably connected to the housing, where the slider has the first member and/or the second member connected thereto, and where the housing comprises a connector configured to removably connect the housing to a control section of an endoscope.

A proximal end of the first member may be connected to the slider and a proximal end of the second member is connected to the housing. The connector may be sized and shaped to longitudinally slide on to a deflection control lever of the control section of the endoscope. The connector may be sized and shaped to resiliently snap on to a deflection control lever of the control section of the endoscope.

An example embodiment may be provided in a medical apparatus comprising an endoscopic tool comprising first and second members longitudinally slidable relative to each other; and a control connected to a proximal end of the endoscopic tool, where the control comprises a housing and an actuation mechanism, where the actuation mechanism is connected to the housing, where the actuation mechanism has the first member and/or the second member connected thereto, and where the housing comprises a connector configured to removably connect the housing to a deflection control lever of an endoscope.

The first member may comprise a sheath and the second member comprises basket device. A proximal end of the sheath may be connected to the actuation mechanism and a proximal end of the basket device is connected to the housing. A proximal end of the basket device may be connected to the actuation mechanism and a proximal end of the sheath is connected to the housing. The connector may be sized and shaped to longitudinally slide onto the deflection control lever of a control section of the endoscope. The connector may be sized and shaped to resiliently snap onto the deflection control lever of a control section of the endoscope. A connection of the first member and/or the second member to the actuation mechanism may comprise a rack and pinion configuration. A connection of the first member and/or the second member to the actuation mechanism may comprise a pivoting member. A connection of the first member and/or the second member to the actuation mechanism may comprise a spring member. The spring member may comprise a "V" shape.

An example method may comprise inserting a distal end of an endoscopic device into a working channel of an endoscope, where the endoscopic device comprises an endoscopic tool, where the endoscopic tool comprises first and second members which are longitudinally slidable relative to each other; and removably connecting a proximal end of the endoscopic device to a deflection control lever of a control section of the endoscope, where the proximal end comprises a housing and an actuation mechanism, where the actuation mechanism is slidably connected to the housing, where the actuation mechanism has the first member and/or the second member connected thereto, and where the housing comprises a connector which removably connects the housing to the control section of the endoscope.

The first member may comprise a sheath and the second member comprises basket device, where inserting the distal end of the endoscopic device into the working channel of the endoscope comprises inserting distal ends of the sheath and the basket device into the working channel. Removably connecting the proximal end of the endoscopic device to the deflection control lever of the control section of the endoscope may comprise longitudinally sliding the housing on to the deflection control lever. Removably connecting the proximal end of the endoscopic device to the deflection control lever of the control section of the endoscope may comprise resiliently snapping the housing onto to the deflection control lever.

An example method may comprise providing an endoscopic tool, where the endoscopic tool comprises first and second members which are longitudinally slidable relative to each other; and connecting a control to a proximal end of the endoscopic tool, where the control comprises a housing and an actuation mechanism, where the actuation mechanism is longitudinally slidably connected to the housing, where the actuation mechanism has the first member and/or the second member connected thereto, and where the housing comprises a connector configured to removably connect the housing to a deflection control lever of a control section of an endoscope.

A proximal end of the first member may be connected to the actuation mechanism and a proximal end of the second member may be connected to the housing. The connector may be sized and shaped to longitudinally slide onto the deflection control lever of the control section of the endoscope. The connector may be sized and shaped to resiliently snap onto the deflection control lever of the control section of the endoscope.

An example embodiment may be provided in a medical apparatus comprising an endoscope comprising a bending portion and a handle portion; an endotherapy device having an effecter part and at least one control wire connected to the effecter part; a coupling portion connecting the endotherapy device to the endoscope, wherein the coupling portion is configured to extend the control wire along a surface of the handle portion; a control lever located at the handle portion and configured to linearly move in a first direction for controlling the bending section; and an actuation mechanism located and configured to linearly move in a second direction on the control lever, wherein the actuation mechanism includes a connecting portion configured to connect a proximal end of the control wire for controlling the effecter part.

An example embodiment may be provided in a medical apparatus comprising an endoscopic tool comprising first and second members longitudinally slidable relative to each other; and a control connected to a proximal end of the endoscopic tool, where the control comprises a housing and an actuation mechanism, where the actuation mechanism is connected to the housing, where the actuation mechanism has the first member and/or the second member connected thereto, and where the housing comprises a connector configured to removably connect the housing to a deflection control lever of an endoscope, wherein the actuation mechanism is a joystick control which is capable of movement in a first direction and capable of movement in a second direction, wherein movement in a first direction provides actuation of a first member and wherein movement in a second direction provides actuation of a second member. The joystick control may be connected to a stiff flexible cable routed through a conduit for actuation of a first member through movement of the joystick in a first direction.

An example method may comprise inserting a distal end of an endoscopic device into a working channel of an endoscope, where the endoscopic device comprises an endoscopic tool, where the endoscopic tool comprises first and second members which are longitudinally slidable relative to each other; and removably connecting a proximal end of the endoscopic device to a deflection control lever of a control section of the endoscope, where the proximal end comprises a housing and an actuation mechanism, where the actuation mechanism is slidably connected to the housing, where the actuation mechanism has the first member and/or the second member connected thereto, and where the housing comprises a connector which removably connects the housing to the control section of the endoscope, wherein the actuation mechanism is a joystick control which is capable of movement in a first direction and capable of movement in a second direction, wherein movement in a first direction provides actuation of a first member and wherein movement in a second direction provides actuation of a second member.

An example method may comprise providing an endoscopic tool, where the endoscopic tool comprises first and second members which are longitudinally slidable relative to each other; and connecting a control to a proximal end of the endoscopic tool, where the control comprises a housing and an actuation mechanism, where the actuation mechanism is longitudinally slidably connected to the housing, where the actuation mechanism has the first member and/or the second member connected thereto, and where the housing comprises a connector configured to removably connect the housing to a deflection control lever of the control section of an endoscope, wherein the actuation mechanism is a joystick control which is capable of movement in a first direction and capable of movement in a second direction, wherein movement in a first direction provides actuation of a first member and wherein movement in a second direction provides actuation of a second member.

It should be understood that the foregoing description is only illustrative. Various alternatives and modifications can be devised by those skilled in the art. For example, features recited in the various dependent claims could be combined with each other in any suitable combination(s). In addition, features from different embodiments described above could be selectively combined into a new embodiment. Accordingly, the description is intended to embrace all such alternatives, modifications and variances which fall within the scope of the appended claims.

What is claimed is:

1. A medical apparatus comprising:
   an endoscopic tool comprising first and second members longitudinally slidable relative to each other;
   a control housing comprising a connector configured to removably connect to a proximal end of an endoscope, where the connector comprises a portion which is deflectable and configured to resiliently snap onto a deflection control lever at the proximal end of the endoscope, the deflection control lever extending external to an outermost surface of the endoscope for engagement by a user and operably coupled to an actuator disposed internally within the endoscope, the deflection control lever configured to control deflection of a distal end of the endoscope away from a longitudinal axis of the endoscope; and
   a control actuation mechanism on the control housing, where the control actuation mechanism is in mechanical communication with the second member and configured to actuate the second member to capture biological material;
   where the first member comprises a sheath, and where the control actuation mechanism is configured to allow for deflection of the distal end of the endoscope and at least one of actuation of a basket on the second member or actuation of the sheath with a single finger of a user.

2. A medical apparatus of claim 1, wherein a proximal end of the sheath is connected to the control actuation mechanism and a proximal end of the basket device is connected to the control housing.

3. A medical apparatus of claim 1, wherein a proximal end of the basket device is connected to the control actuation mechanism and a proximal end of the sheath is connected to the control housing.

4. The medical apparatus as claimed in claim 1 where the control actuation mechanism comprises a joystick.

5. The medical apparatus as claimed in claim 4 where the control actuation mechanism is configured move the second member when the joystick is moved in a first direction, and where the control actuation mechanism is configured to move the first member when the joystick is moved in a second direction orthogonal to the first direction.

6. The medical apparatus as claimed in claim 1 where the control actuation mechanism is configured move the second member relative to the first member when a portion of the control actuation mechanism is moved in a first direction, and where the control actuation mechanism is configured to move the first member relative to the second member when the portion of the control actuation mechanism is moved in a different second direction.

7. The medical apparatus as claimed in claim 6 where the second direction is orthogonal to the first direction.

8. The medical apparatus as claimed in claim 1 where the control actuation mechanism is configured to longitudinally slide the second member relative to the first member, and where the second member extends through the first member.

9. The medical apparatus as claimed in claim 1 where the control actuation mechanism comprises a linkage for moving a roller, where the roller is coupled to the first member, where the control actuation mechanism is configured to move the first member.

10. An apparatus comprising:
    a control housing comprising a connector configured to removably connect to a proximal end of an endoscope, where the connector defines an inner surface sized and shaped to mate with an outer surface of a deflection control lever and comprises a portion which is deflectable and configured to resiliently snap onto the deflection control lever, the deflection control lever extending external to an outermost surface of the endoscope for engagement by a user and operably coupled to an actuator disposed internally within the endoscope, where movement of the control housing relative to the endoscope is configured to cause a corresponding movement of the deflection control lever to control deflection of a distal end of the endoscope away from a longitudinal axis of the endoscope; and
    a control actuation mechanism attached to the control housing, where the control actuation mechanism is configured to actuate a retrieval device comprising a sheath and a basket to capture biological material, and where the control housing and the attached control actuation mechanism are configured to allow for deflection of the distal end of the endoscope, actuation of the basket, and actuation of the sheath with a single finger of a user.

11. A medical apparatus comprising:
    an endoscope extending along a longitudinal axis and comprising:
       a deflection control lever extending external to an outermost surface of the endoscope at a location adjacent to a proximal end of the endoscope for engagement by a user, the deflection control lever operably coupled to an actuator disposed internally within the endoscope and configured to control deflection of a distal end of the endoscope away from the longitudinal axis;

a control housing including a connector for removably attaching the control housing to the endoscope, the connector defining an inner surface sized and shaped to mate with an outer surface of the deflection control lever and comprising a portion which is deflectable and configured to resiliently snap onto the deflection control lever at the proximal end of the endoscope such that movement of the control housing causes a corresponding movement of the deflection control lever to control deflection of the distal end of the endoscope; and a control actuation mechanism in the control housing, the control actuation mechanism comprising a joystick configured to actuate a retrieval device to capture biological material, where the control actuation mechanism is configured to longitudinally slide a second member of the retrieval device relative to a first member of the retrieval device when the joystick is moved in a first direction, where the control actuation mechanism is configured to move the first member of the retrieval device when the joystick is moved in a second direction orthogonal to the first direction, where the second member extends through the first member, where the first member is a sheath and the second member comprises a basket, and where the control housing and the control actuation mechanism are configured to allow for deflection of the distal end of the endoscope, movement of the basket relative to the sheath, and movement of the sheath with a single finger of a user.

* * * * *